United States Patent [19]

Villa-Real

[11] 4,320,767
[45] Mar. 23, 1982

[54] POCKET-SIZE ELECTRONIC CUFFLESS BLOOD PRESSURE AND PULSE RATE CALCULATOR WITH OPTIONAL TEMPERATURE INDICATOR, TIMER AND MEMORY

[76] Inventor: Antony-Euclid C. Villa-Real, 2512 Capistrano Ave., Las Vegas, Nev. 89121

[21] Appl. No.: 137,607

[22] Filed: Apr. 7, 1980

[51] Int. Cl.³ .............................................. A61B 5/02
[52] U.S. Cl. .................................................. 128/680
[58] Field of Search ............... 128/678, 680, 681, 687, 128/689, 690, 736, 662

[56] References Cited

U.S. PATENT DOCUMENTS

| | | | |
|---|---|---|---|
| 1,675,799 | 7/1928 | Goldschmidt | 128/689 |
| 3,032,030 | 5/1962 | Han | 128/678 |
| 3,349,623 | 10/1967 | Pastan | 128/678 |
| 4,245,648 | 1/1981 | Trimmer et al. | 128/680 |

*Primary Examiner*—William E. Kamm

[57] ABSTRACT

Several related preferred embodiments pertaining to a non-invasive type of pocket-size electronic cuffless blood pressure and pulse rate calculator with optional temperature indicator, timer and memory are disclosed, for fast, accurate and reliable determination of both systolic and diastolic blood pressure values of the human or animal subject utilizing the "Korotkoff method" of detection; pulse rate being determined independently or in conjunction with the blood pressure measurement; said device utilizing microcomputers and light-emitting display means such as, but not limited to, LED or LCD pressure display gauge representing the equivalence in millimeters of Hg. a range from 0 to 300. This disclosure is characterized by several models of compact construction and modernistic designs with minimal moving mechanical parts and with a preferrably linearly displaceable pressure head applying means for on-the-spot over-the-artery application, coupled with an optimally located acoustical transducer for detecting the "Korotkoff sounds" created during the process of extravascular and occlusion and gradual deocclusion of the subjected pressurized artery; the device has a manually or electronically operable pressure threshold that can be set about 30 millimeters Hg. equivalence or more above the anticipated systolic pressure, and said pressure threshold capable of being entered into the microcomputer's memory to effect the automatic triggering of the systolic and diastolic electronic sensing and latching of the desired blood pressure data only after said pressure threshold has been reached.

52 Claims, 23 Drawing Figures

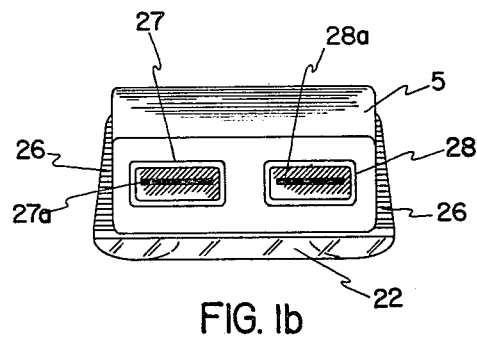
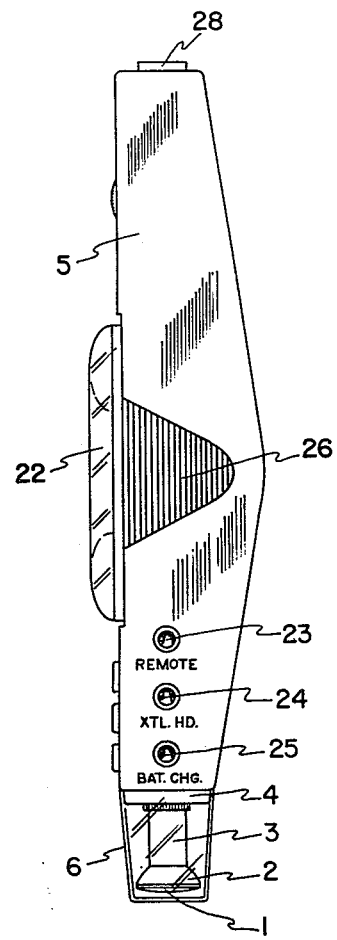
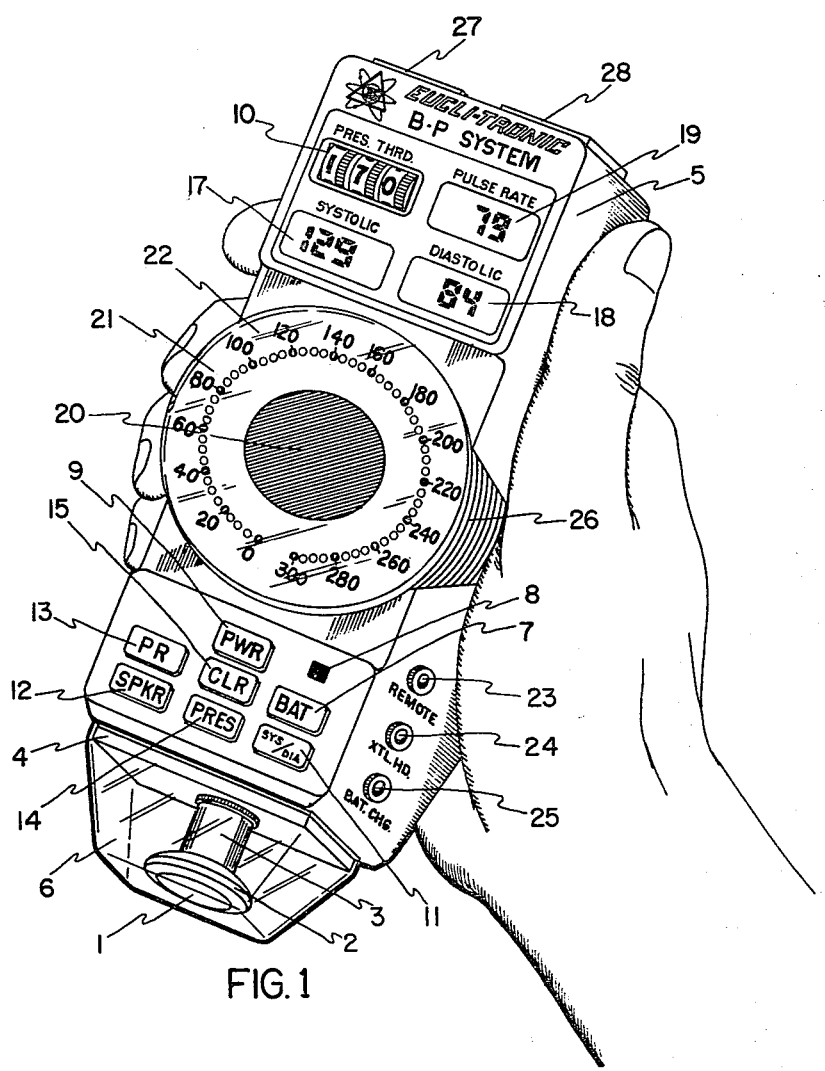
FIG. 1b
FIG. 1a
FIG. 1

POCKET-SIZE ELECTRONIC CUFFLESS BLOOD PRESSURE AND PULSE RATE CALCULATOR WITH OPTIONAL TEMPERATURE INDICATOR, TIMER AND MEMORY

BACKGROUND OF THE INVENTION

It is presented here that even though the use of the inflatable-deflatable compression arm-cuff working in conjunction with the rubber bulb, the air-valve regulator, and either the mercury or aneroid manometer has been widely accepted for several decades to achieve the non-invasive clinical measurements of human blood pressure, it has been found to have many disadvantages because of the following reasons:

(1) Longer time frame involved in the operation of the device causing pain, numbness and tingling sensations on the part of the subject experiencing the said sensations below the compression area of the pressurized limb such as the upper arm.

(2) Unnecessary prolonged periods of repeated extravascular compression causing blood flow impedance, not only to the venous blood return from below the compression area, but also to the general arterial and capillary circulatory vessels therearound the said compression points.

(3) The compression arm-cuff, having a constant width, is not always optimally applicable to a variety of arm diameters of various individuals thus causing erroneous results.

(4) If the arm-cuff has been placed too loosely around the limb, such as the upper arm, there results an erroneously high reading.

(5) If the arm-cuff is placed around the upper arm too tightly, there results a significant low reading of the blood pressure measurement.

(6) The arm-cuff is time-consuming and awkward to manipulate, especially for self application by the subject, or by application of others to the patient.

(7) The air-valve regulator sometimes gets stuck, thus there is danger of having a prolonged period of arm-cuff compression therearound the subject's limb until the stuck air-valve has been loosened.

(8) The arm-cuff and the associated rubber bulb and air-valve regulatory mechanism add more cost and greater bulk to the device, and the tubings coordinating them to the mercury or aneroid gauges sometimes get entangled during the operation of the device.

For these reasons, the instant invention has been invented to help solve the disadvantages of the blood pressure device utilizing the said compression arm-cuff and associated regulatory mechanisms, and to solve a tremendous demand by the public for a more portable, fast, and cuffless blood pressure system integrated with the most advanced electronic micro-circuitry with data-time-date memory entry and retrieval, so that a device such as this can bring forward right at the fingertips of the users around the world, an easily operable and informative device that is reliable and accurate for both self-application and applications to others in the hospitals, clinics, doctors offices, and most especially, for home use and during travel, because hypertension afflicts a large segment of the worldwide population, being the top ranking disabling and killer ailment of this century.

In the United States alone, according to the estimates of the National Heart, Lung, and Blood Institute, there are about 35 million Americans with definite hypertension and approximately 25 million Americans having borderline hypertension.

In accordance with the 1978 data from the National Center of Health statistics; National Heart, Lung, and Blood Institute; National Cancer Institute; American Cancer Society; Arthritis Foundation and the National Institute of Arthritis, Metabolism and Digestive Diseases, hypertension is the most prevalent of the chronic diseases (in millions of patients) as compared to other chronic diseases such as arthritis, heart disease, mental illness, visual impairment, spine impairment, chronic bronchitis, asthma, diabetes, stomach ulcer, and cancer.

According to the 12-year study by the Public Health Service in Framingham, Mass., wherein 5,209 men and women ranging from the ages of 35 to 74 were examined, and the health records of those with high blood pressure and those having normal blood pressure comparatively analyzed, 3 important findings resulted:

(1) Those with high blood pressure had more than 6 times as many heart failures.

(2) More than seven times as many strokes compared with those having normal blood pressure readings.

(3) 3 times as many heart attacks compared to the normal blood pressure group.

It is, therefore, very important that since hypertension causes many serious and frequently fatal complications, and that since it is usually a "silent" or asymptomatic disease developing for relatively longer periods, it is of utmost necessity that blood pressure measurements be frequently made in order to assure the population on their current blood pressure readings so as to give the necessary and proper treatment for preventing complications and to prevent the development of the disease by regulatory measures such as a change in lifestyle as well as change in diet.

A. PRIOR ART

The history of recording blood pressure began in 1733 when Stephen Hales published the results of his experiments in which he directly measured the arterial blood pressure of various animals. His experiments were performed using a 9-foot long glass tubing attached to a brass cannula by means of a goose' trachea. The cannula was inserted into the femoral artery of the experimental animal, allowing the blood to rise in the glass tube up to a level equivalent to the animal's systemic arterial blood pressure. This very crude experiment led to the long list of experimentations which eventually advanced to the use of the widely accepted blood pressure measuring devices of the non-invasive type utilizing the so-called Riva-Rocci compression arm-cuff with an inflatable-deflatable rubber bladder placed inside the cuff. However, findings in the use of the said pneumatic cuff pointed toward certain significant errors due to the reasons previously mentioned.

Although there have been significant advances in blood pressure measurements using this indirect non-invasive method with the implementation of the compression arm-cuff, ranging from the purely mechanical and subjective interpretation aided by a stethoscope, to the curent devices requiring no stethoscope at all, but instead, employing audio-visual means with electronic circuitry, the inherent problems encountered in the use of the widely accepted compression arm-cuffs have not yet been properly solved. From the biomedical standpoint, the repetitive circumferential compression of the upper arm causes significant discomfort on the part of the subject who often experiences pain or numbness and tingling sensations below the area of compression due to exposure to a longer time frame during such manipulation.

There have been many patents issued by United States Patent Office, ranging from the crudest to the most sophisticated blood pressure and pulse rate measuring devices, and the majority of the non-invasive or indirect method of blood pressure apparatuses utilize either the mercury manometer or the aneroid manometer in coordination with the compression arm-cuff. There are some inventions that use the doppler effect; some resort to measurement of blood pressure in the ear lobe. Others, especially U.S. Pat. No. 3,391,691 invented by R. W. Young; U.S. Pat. No. 1,673,513, invented by G. L. Jacquot; U.S. Pat. No. 1,900,286 invented by W. I. Huber; Pat. No. 1,637,421 invented by E. W. Lipschutz; U.S. Pat. No. 2,093,337 invented by W. P. Nolan; Pat. No. 2,612,156 invented by C. C. Curtis; U.S. Pat. No. 2,572,389 invented by W. C. Rice; U.S. Pat. No. 1,900,285 invented by W. I. Huber; U.S. Pat. No. 2,833,274 invented by R. J. Reiss; U.S. Pat. No. 3,032,030 invented by P. S. Ham, are either quite crude or too mechanical and none of these enumerated inventions identified by the above-mentioned patent numbers are electronic in nature to effect accurate blood pressure measurements.

There are also blood pressure devices where the finger is the basis for blood pressure measurement, for example, U.S. Pat. No. 3,189,024 invented by P. Smith. Other blood pressure devices are bulky, and using fragile mercury manometers that require a vertical standing position for the mercury column to achieve accuracy. Other devices use aneroid gauges which have many mechanical parts requiring frequent calibration.

BIO-PHYSICO-PHYSIO-PATHOLIGIC BACKGROUND OF THE INVENTION

In order to fully understand the clinical basis of the non-invasive type of blood pressure measurements, it is imperative that one must have a clear understanding not only of the physiology of the cardiovascular system including the hemodynamics of the circulating blood inside the vascular tree, but also, the pathological changes in the body relevant to hypertension, stroke, heart ailment, kidney damage, hemorrhagic disorder, neurologic control, anxiety and nervousness.

The heart is the main pumping organ of the whole cardiovascular system. The entire circulatory system does a tremendous amount of work. It has been found that during rest, blood is pumped around the body at a rate of about five liters per minute, and during excessive exercise, the amount that is pumped can go over 25 liters per minute. A calculation has been made that during a lifetime of an average individual, a total of approximately 500 million liters of blood is pumped and circulated around the body.

Every heart beat is characterized by the contraction of the heart muscles delivering blood into the pulmonary circulation for oxygenating the blood preparatory to transport of oxygen to the systemic circulation to bring forth supply of oxidation requirements of the tissues, while at the same time, effecting the transfer of waste products of cell metabolism from the tissues via the blood stream. For every cardiac contraction, the blood pumped into the systemic circulation through the aorta presents a pressure head force that is responsible for the systolic blood pressure in the main arteries such as the brachial artery located at the upper arm. This pressure head force secondary to this pumping action of the heart exerts pressure into the walls of the brachial artery, a pressure commonly known as the systolic blood pressure. After every heart beat, the cardial muscles relax. This period of relaxation is known as the diastole phase of the cardiac cycle. The low point of intravascular blood pressure within the brachial artery is known as the diastolic blood pressure. The blood pressures vary in the different parts of cardiovascular system, being higher in the arterial circulation and lower in the veins and capillaries. The arterial blood pressure is directly proportional to the relationship between the total cardiac output and total peripheral resistance of the cardiovascular system.

In cases wherein there are variations in temperature conditions, the vascular system responds in such a way that there is a resultant vasoconstriction of the arteries during exposure to cold environment, and a resultant vasodilatation during exposure of the living body to warm or hot temperature.

During fear, anxiety or exposure to stressful conditions, the body produces a hormone called adrenaline which causes the smooth muscles of the arterioles to contract, thereby effecting vasoconstriction, a condition which increases the blood pressure due to increased intravascular peripheral resistance. In kidney damage such as glomerulonephritis, a hormone called renin is released by the kidney as a built-in feedback mechanism to restore the blood flow in the kidney to normal, however, this causes blood pressure to rise as a result of the direct action of a hormone angiotensin II which is triggered by the renin release. As a result of high intake of salt (sodium chloride), there is greater water retention causing increased blood volume, which again, directly and proportionately increases the blood pressure. In the majority of cases where there are elevated levels of cholesterol, triglycerides and low density lipoprotein in the bloodstream existing for prolonged periods of time, an accumulation of fatty deposits occur inside the endothilial walls of the main arteries, especially around the heart, including the coronary arteries that supply blood to the heart muscles. This deposition of fatty plaques in the major arteries causes the development of what is known as atherosclerosis, or hardening of the arteries, which is a primary causative factor in myocardial disease. When there is long-standing increase in the systolic and diastolic blood pressure levels above the accepted normal range, hypertension generally develops towards dangerous complications because of the predisposition of the individual to possible heart attack, stroke, and/or kidney damage. Realizing that hypertension is fatal and so rampant a disease in our society, it is of utmost importance that blood pressure be checked frequently.

On the other hand, there are cases wherein both the systolic and diastolic readings may be lower than the normal range, a condition called hypotension. This may be brought about by a decrease in blood volume such as a significant loss of blood through hemorrhage or other hemorrhagic diseases or due to shock. Blood pressure measurements in these cases, must also be frequently checked in order to properly correlate with the adequate therapeutic procedures aimed towards the assurance and maintenance of the optimally acceptable systolic and diastolic blood pressures in the cardiovascular system for preserving proper cellular oxygenation and carbon dioxide excretion from the cells, as well as the maintenance of the required nutritive requirements of the brain and other vital organs of the body.

There are two methods of blood pressure measurements of the human or animal subject: (1) the direct method which employs the insertion of a cannular probe into the blood vessel, while said probe is connected to a blood pressure measuring apparatus, and (2) the indirect procedure, which is the most widely accepted method in clinical practice that utilizes the compression arm-cuff with the associated components. The latter senses for the "Korotkoff sounds" created by the acoustical turbulence of blood flow through the compressed semi-opened artery such as the brachial artery. When the brachial artery is fully compressed by the arm-cuff, there is no sound detected because of the absence of arterial blood flow below the fully occluded portion of the said compressed artery. As the arm-cuff pressure is gradually released from that state of compression and total arterial occlusion, each cardiac systole delivers an arterial pressure head force that becomes propagated through the semi-opened artery until the critical resistance exerted by the intravascular wall is exceeded by the said arterial pressure head force, at which instant, the first sharp "thud" sound of "Korotkoff" is detected, thereby determining the systolic reading in relation to the millimeters of Hg. of applied cuff pressure registered in the pressure gauge. As the compressed artery undergoes continuous gradual decompression, the "Korotkoff" sounds follow five phases of characteristically differential sounds; (1) first phase characterized by the aforementioned sharp "thud" sound; (2) a second phase characterized by blowing or swishing sounds; (3) a third phase characterized by a softer thud sound than phase 1; (4) a fourth phase with a soft and blowing sound that disappears and; (5) a fifth phase when the sounds completely disappear. The occurrence of the fifth phase is the commonly acceptable diastolic blood pressure reading in the cases wherein only one diastolic measurement is taken. The fourth phase is considered to have certain disadvantages when used to indicate the diastolic level.

SUMMARY OF THE INVENTION

The main object of the present invention is to provide a pocket-size portable cuffless electronic blood pressure and pulse rate calculator. utilizing a directly applicable on-the-spot over the artery compression and decompression pressure head applying means integrated with an acoustical sensing transducer that can eliminate the need for the time-consuming and error-prone compression arm-cuff with a rubber bulb coordinated with an adjustable air-valve that is widely used in most blood pressure clinical measurements.

Another object is to provide a faster, reliable and accurate blood pressure and pulse rate device that uses LED or LCD pressure display gauge capable of eliminating the presently used aneroid pressure gauge that has many mechanical parts needing frequent calibrations, as well as having the capability of replacing the fragile mercury manometers used in most doctor's offices, clinics, laboratories and hospitals.

Another object of the present invention is to provide an advanced system having pressure threshold setting means to effect conservation of electrical energy by triggering the activity of the micro-electronic circuitry for the measurement of the systolic and diastolic blood pressures as well as the pulse rate when in the pressure measuring mode, only after the pressure exerted by the optimally placed pressure head applying means upon the subject's arm has exceeded the manually or electronically set pressure threshold setting.

And yet another object of the invention is to provide an advanced system using micro-electronic circuitry, having analog and digital display means for use in both individual and multi-individual blood pressure and pulse rate calculations, and, equipped with coding means to effect proper entry of date-time-data respective to each individual being tested, and capable for retrieval of the corresponding information from the micro-computer's memory bank; the respective information retrieved, being systematically recalled in either forward or backward sequential order by the use of special function keys.

And yet a further object of the invention is to provide an advanced system using micro-electronic integrated circuitry and having analog and digital visual display means coordinated with audio amplification capabilities for easy triple verification of relevant data.

Still a further object of the invention is to provide a blood pressure device using the indirect non-invasive "Korotkoof" method of measurement without subjecting the patient to the uncomfortable circumferential compression and decompression of the upper arm thereby preventing the undesirable pain, numbness and tingling sensations currently experienced by the subject using the conventional blood pressure devices with compression arm-cuff.

And still another object of the same invention is to provide a reliable compression-decompression integral means of a linearly displaceable piston-type pressure head applying structure with factory set spring load that can compare in accurate pressure calibration with the optimally set equivalent pressure per millimeter of mercury, ranging from 0-300 millimeters Hg; said linear displacement of said pressure head applying structure working electronically in conjunction with a pressure transducer means to bring forth activation of the proper pressure display of LED or LCD type having analog signaling representation depending upon the degree of compression or decompression of the tissues over and above the subjected artery such as the brachial artery.

Yet another object of the present invention is to provide a fast, accurate and reliable data measurement of both blood pressure and pulse rate for easy self-application in the home, office and during travel, as well as for the easy and effective instant measurement of the same by medical personnel.

Moreover, a still further object is to provide a modern blood pressure and pulse rate calculator for use by athletes in the determination of their cardiovascular responses to various degrees of exercise compared to the readings during their relaxed conditions.

Another object is to provide an approximate visual range locator in the analog pressure display gauge, wherein the range between the subject's systolic and diastolic blood pressure, can be seen as a series of continuously latched strand of lighted LED or LCD display as an additional feature of the device for the convenience of the user.

A further object is to provide a device that is capable of logging into the microcomputer's memory, the correct limb location where the blood pressure has been taken, at a specific time and date, and capable of retrieving said data from the memory to the display register.

Another further object is to provide a pocket-size portable blood pressure and pulse rate calculator, having a coordinated function for synthesized speech as well as magnetic card entry and retrieval system.

Yet another object of the instant invention is to provide means for logging into the device, the levels of both the physical activity and the emotional stress of the tested individual, as well as the retrieval of these data at some future time, in conjunction with other entered data, respective to the I.D. number, date, and time which the user desires to retrieve.

Still another object is to incorporate a flashlight means in some embodiments of the invention for illumination purposes.

An additional object of the same invention is to provide a device that can be interconnected to a temperature measuring probe and capable of displaying said temperature data of an individual or multiplicity of patients according to the I.D. number, said data capable of being stored and retrieved to and from the microcomputer's memory in accordance with the date and time of said data measurement.

And still a further object of the present invention is to provide a corresponding step-up auxiliary unit capable of being adapted to a simpler model, to integrate with the said system, thereby enabling the simpler device to function as an advanced sophisticated model, while attaining coordinated systematic and effective functional capabilities.

And yet another object of the present invention is to provide a device that can be used as an electronic stethoscope for diagnosing the respiratory conditions of patients and to diagnose the heart murmurs and cardiac irregularity of heart patients, and also to determine the normality of the respiratory and heart conditions of healthy individuals.

BRIEF DESCRIPTION OF ILLUSTRATIVE DRAWINGS

FIG. 1 is a perspective elevational view of one embodiment of the device having LED pressure gauge showing the right hand in engaging relationship with the device.

FIG. 1a is the side elevational view of FIG. 1.

FIG. 1b is the top elevational view of FIG. 1.

Figure 4:
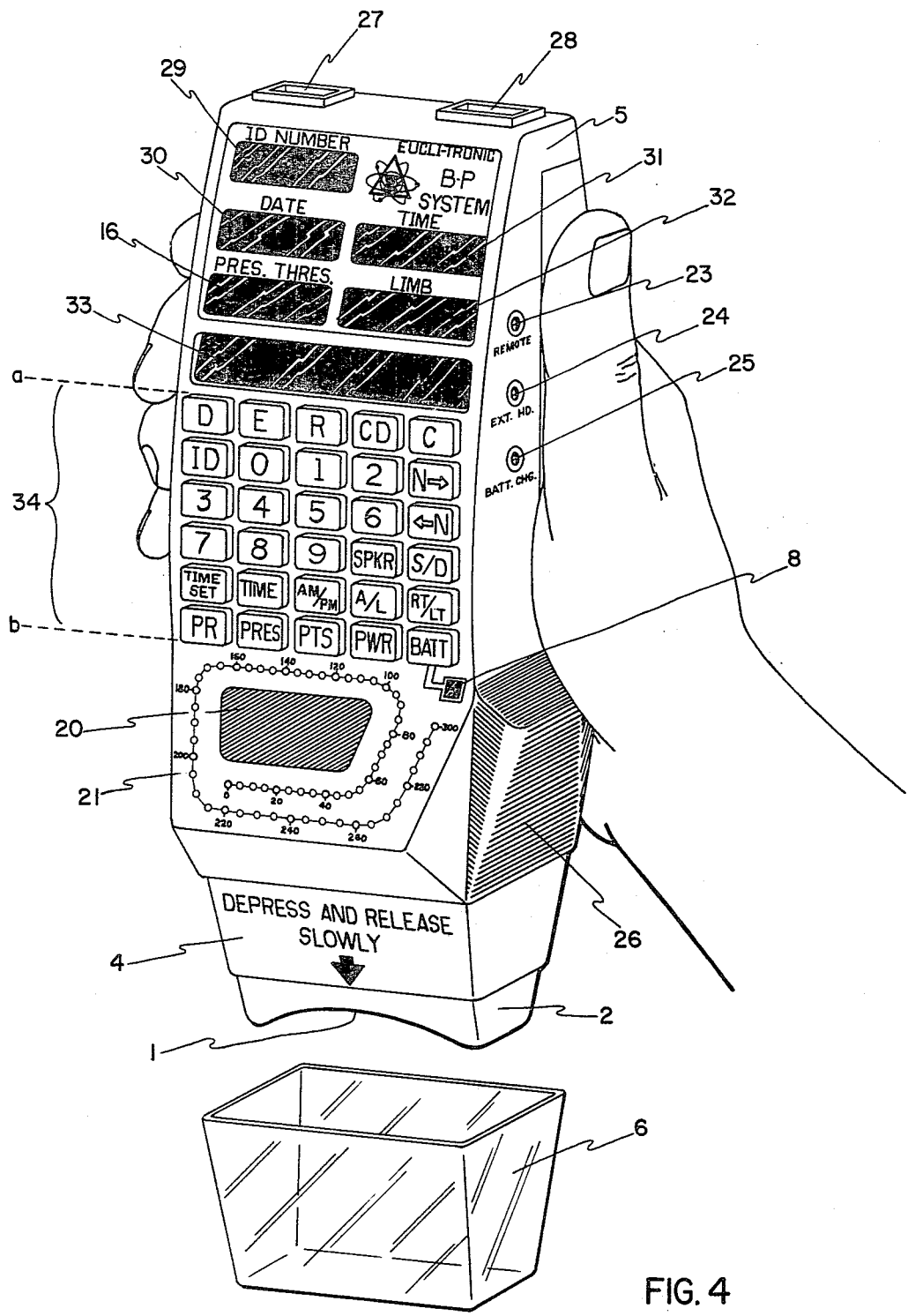

FIG. 4 is another perspective elevational view of another embodiment of the invention that is more sophisticated than the first, and showing a definite design adaptable for multiple individual use and illustrating the various display registers as well as the function keys including a wrap-around pattern of LED display as one form of a pressure gauge surrounding the speaker. Also shown, is the disengaged cover and a right hand in proper engaging relationship with the device. Other connector sockets are shown at the side. The pressure head applying means is found at the bottom portion of the device.

Figure 5:
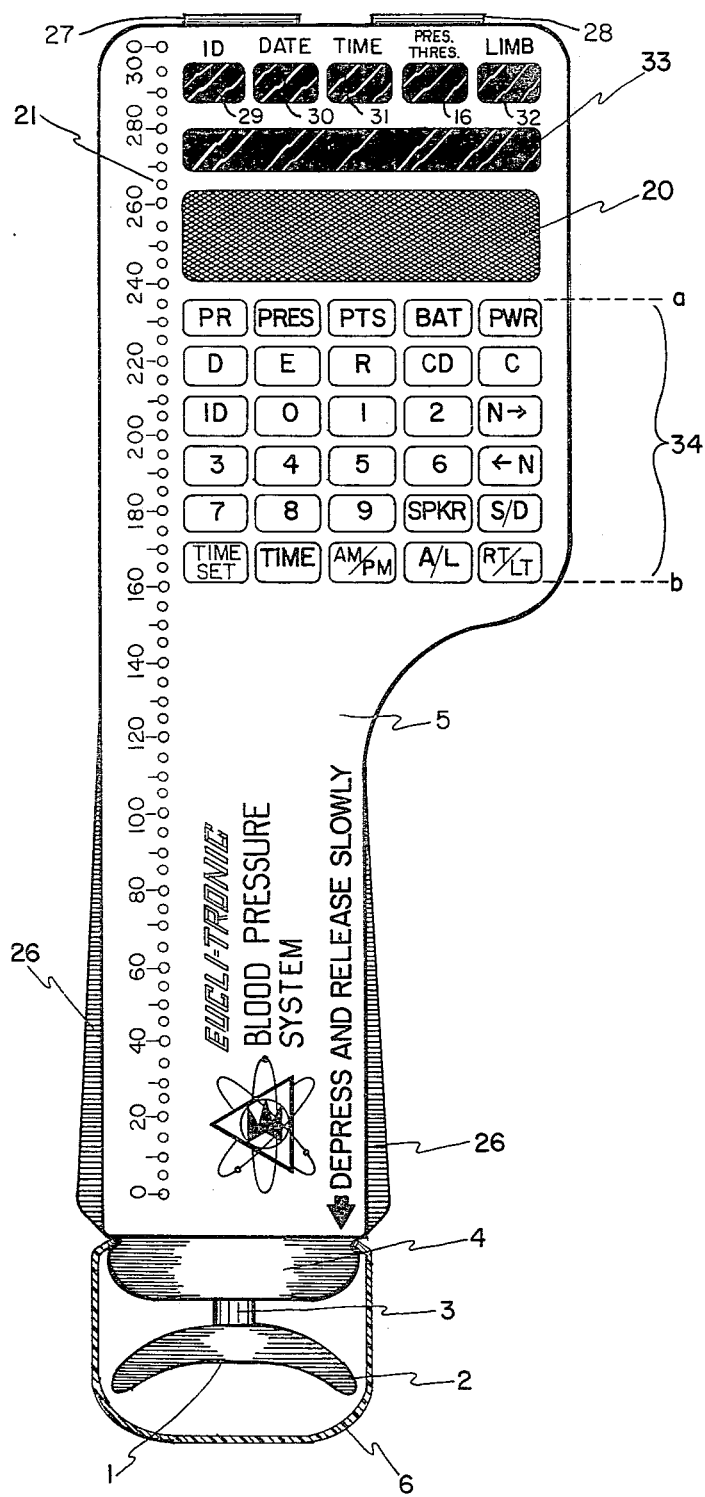

FIG. 5 is another embodiment of the device having a specially designed frame with the same display register elements and function keys as in FIG. 4, but with a straightly aligned LED pressure display gauge and a pressure head applying means of an arc-like special design.

Figure 6:
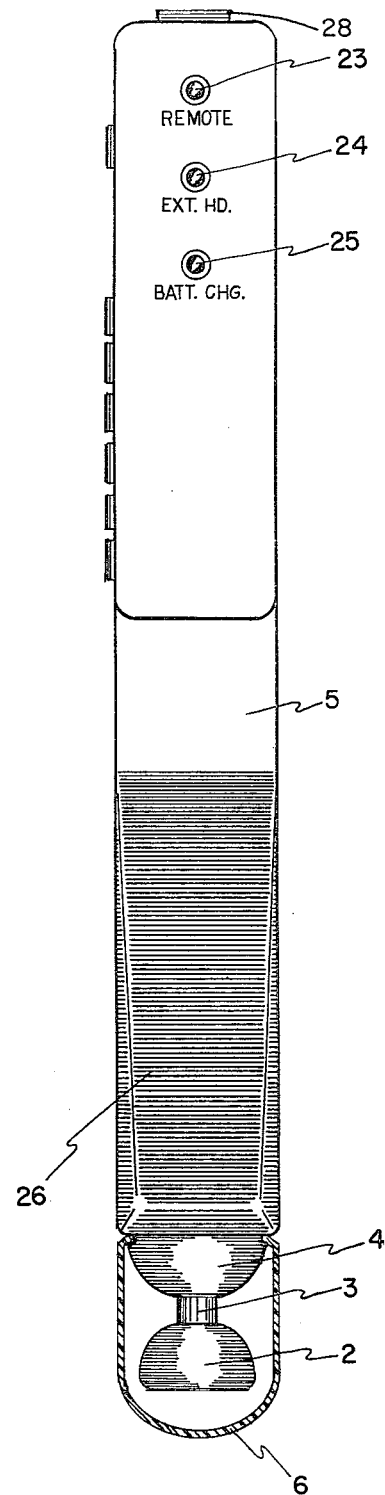

FIG. 6 is the side elevational view of the device of FIG. 5 showing the protective cap in section covering the pressure head applying means. The various connector sockets are shown at the side.

Figure 7:
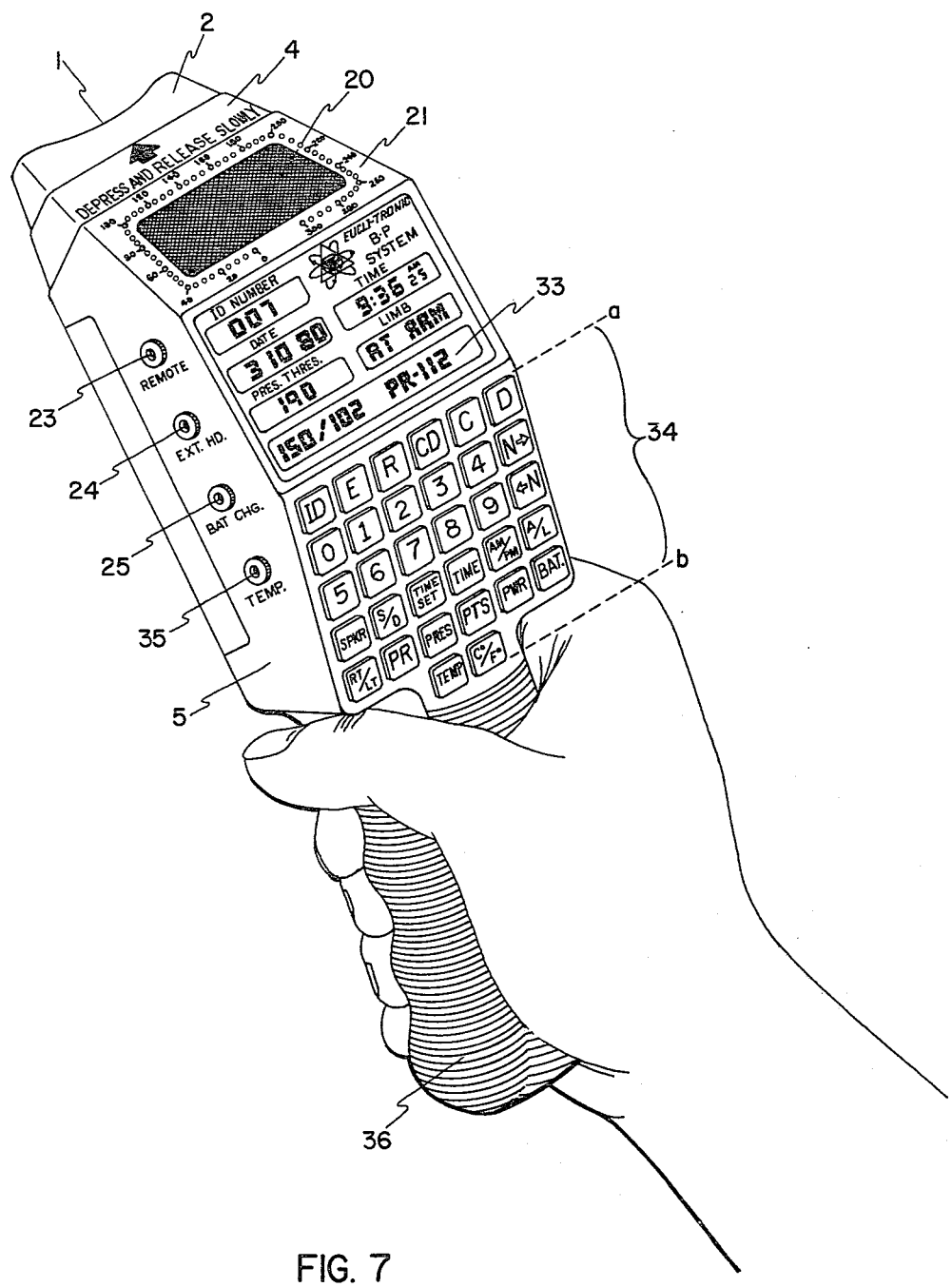

FIG. 7 is an embodiment of the invention for hospital and nursing home use, for greater ease of application by one individual to another. It emphasizes a pistol-grip type portion of the hand-held device. This is shown in the perspective elevational view illustrating a combination of the left side and the front face of the device. Also shown is a fourth connector socket for temperature, plus another function key for temperature, having two positions, one for degrees centigrade and the other for degrees fahrenheit. It emphasizes the LED pressure display gauge patterned in a rectangular fashion around the speaker.

Figure 8:
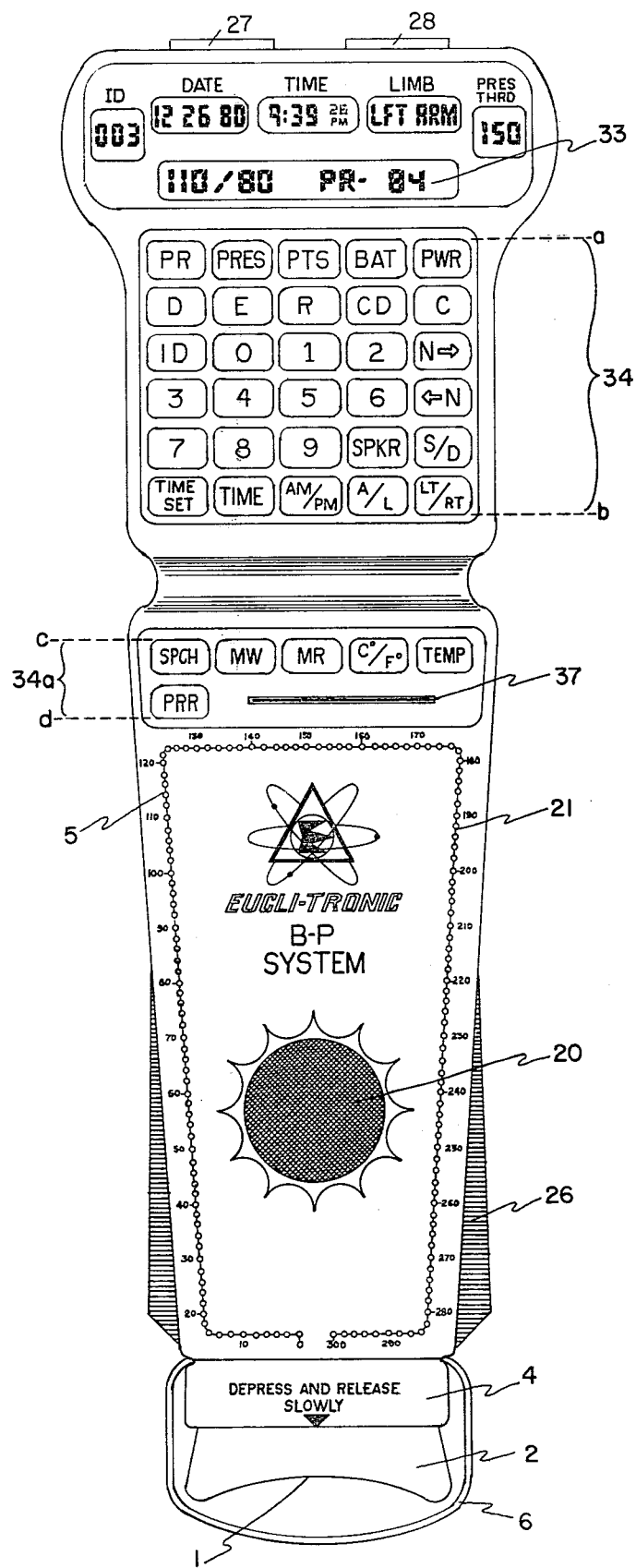

FIG. 8 is a front elevational view of another specially designed embodiment of the device, including the proper display registers, plus additional function keys for speech, memory write, memory read, temperature key for centigrade or fahrenheit, a pulse rate regularity key and a slot for magnetic card entry. The LED pressure display gauge is shown at the lower face surrounding the speaker. The pressure head applying means is covered by the corresponding transparent plastic cap shown in section.

Figure 8A:
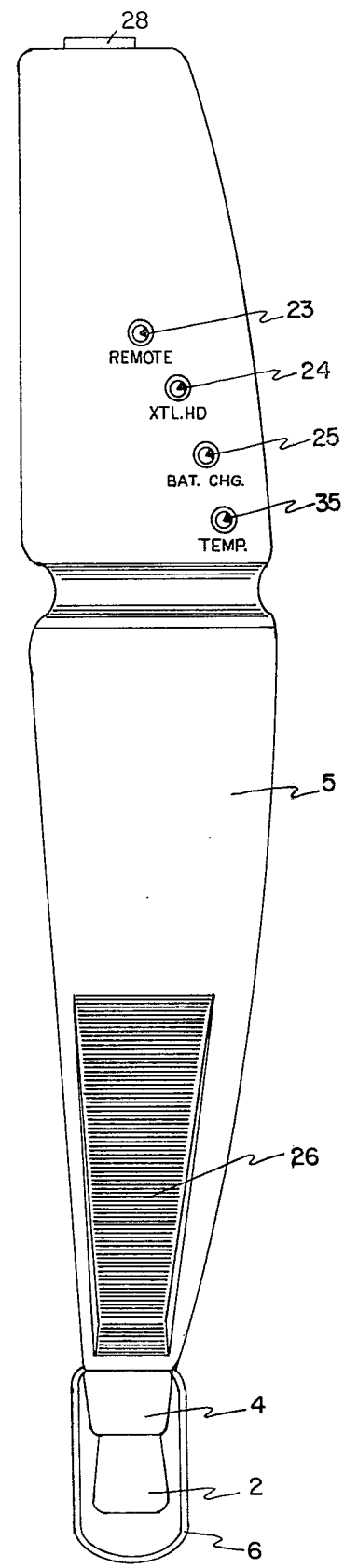

FIG. 8a is the side elevational view of FIG. 8 showing the gripping portion, and the cap engaged in covering position protecting the pressure head applying means.

Figure 9:
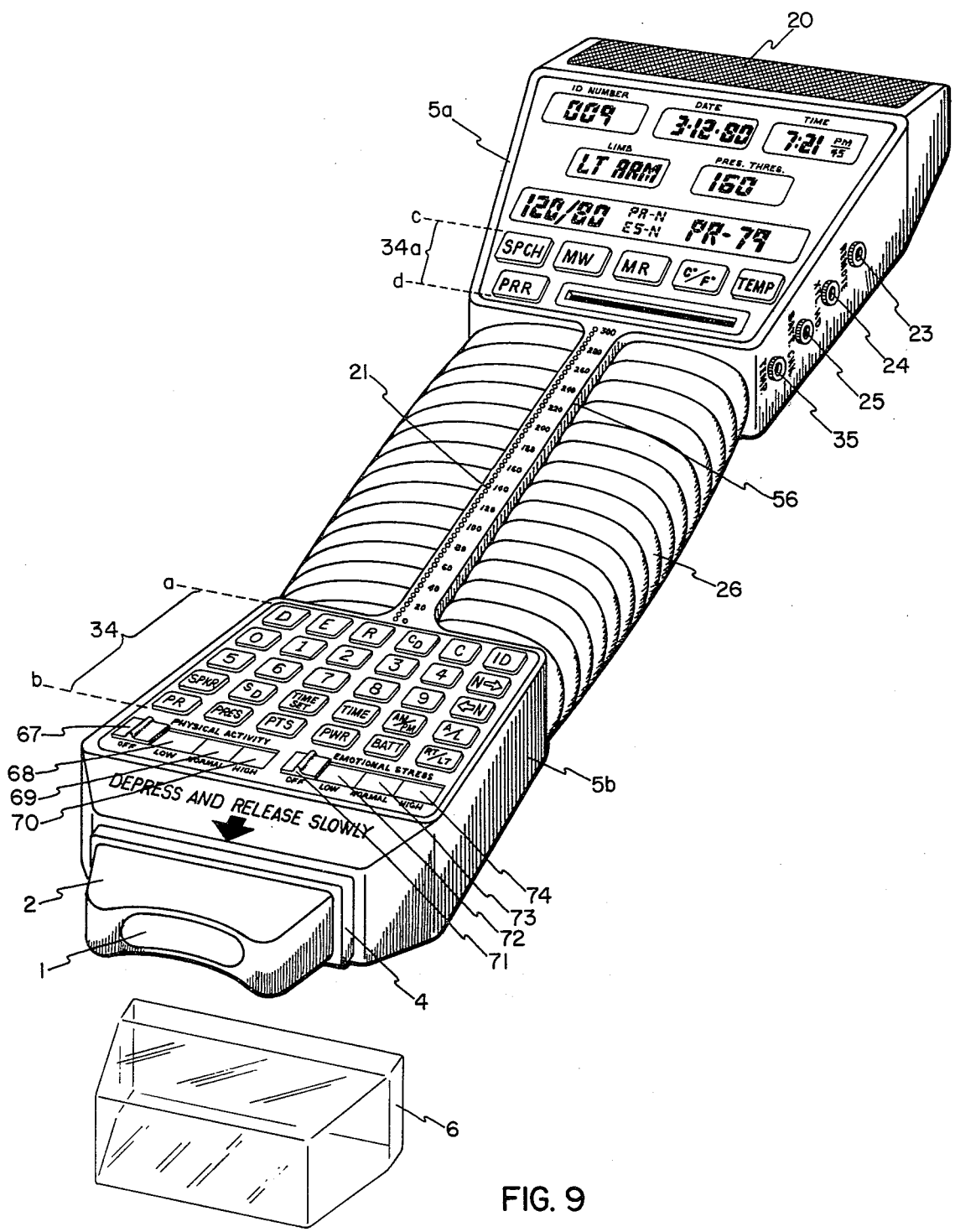

FIG. 9 is a perspective elevational view of yet another embodiment of the instant invention, having a generally similar appearance as that of a home telephone receiver and transmitter segments, interposed between a hand gripping portion which contains the LED pressure display gauge found centrally.

Figure 10:
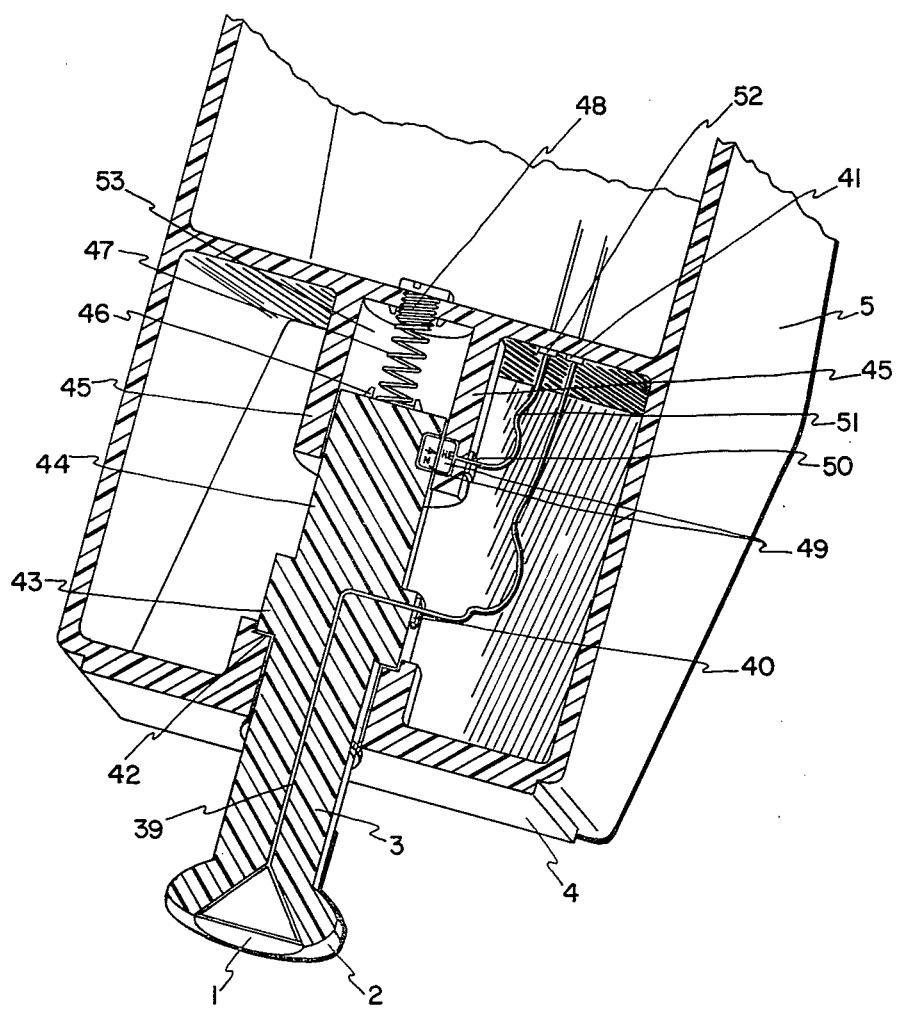

FIG. 10 is the enlarged perspective and sectional view of the internal framework of the pressure head applying means including the coordinating Hall-effect transducer, acoustical transducer, the factory adjusted linear spring load, the piston type linearly movable intermediary component of the pressure head applying means, and including the low resistance electrical wiring.

Figure 11:
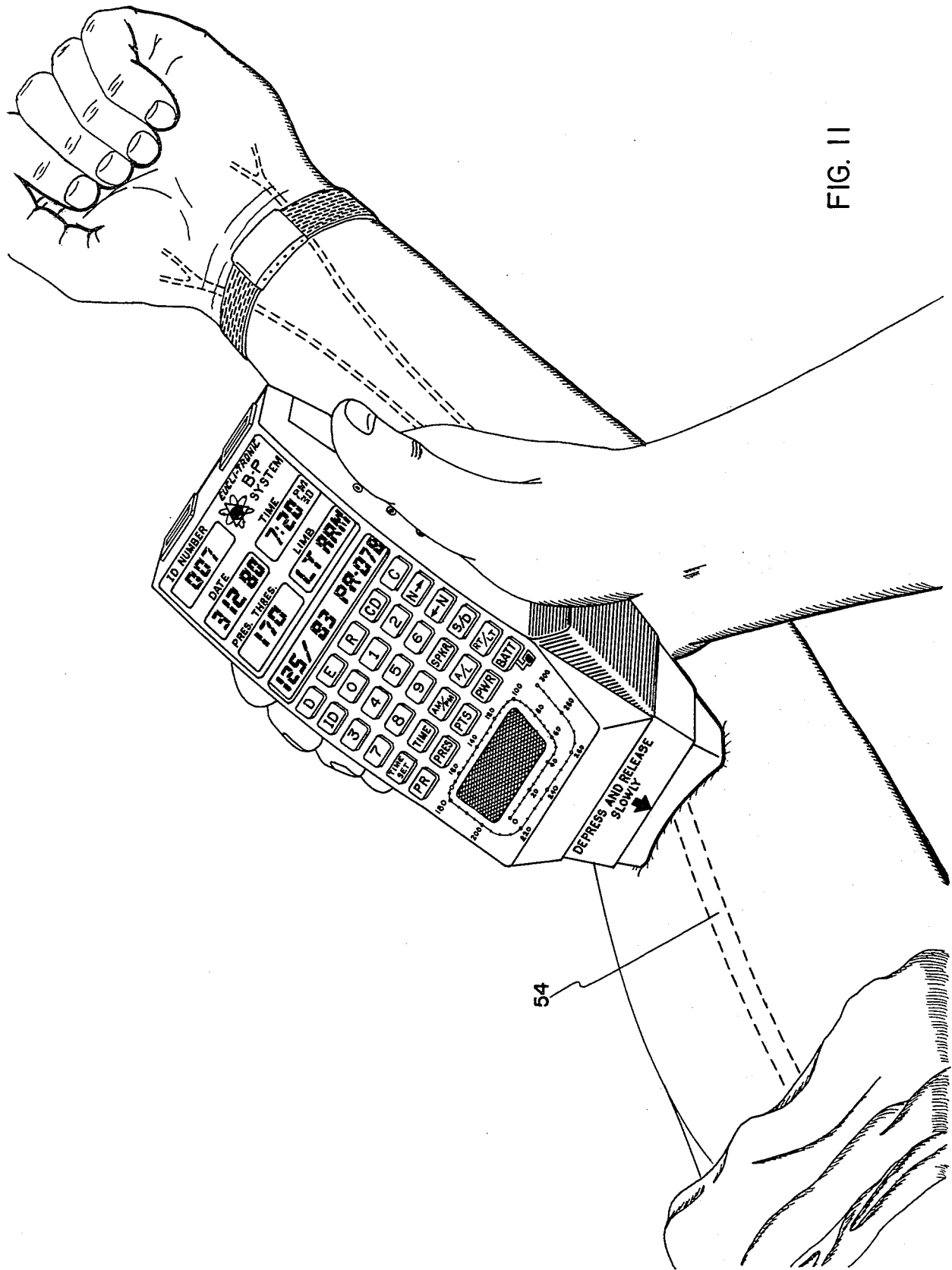

FIG. 11 is the illustration on the embodiment of the device shown in FIG. 4 being applied for blood pressure and pulse rate measurement, wherein the pressure head applying means is engaged in a compression-decompression operation upon the bicep portion of the left upper arm over the brachial artery. As demonstrated, the device is handheld and applied in engaging position by the right hand.

Figure 12:
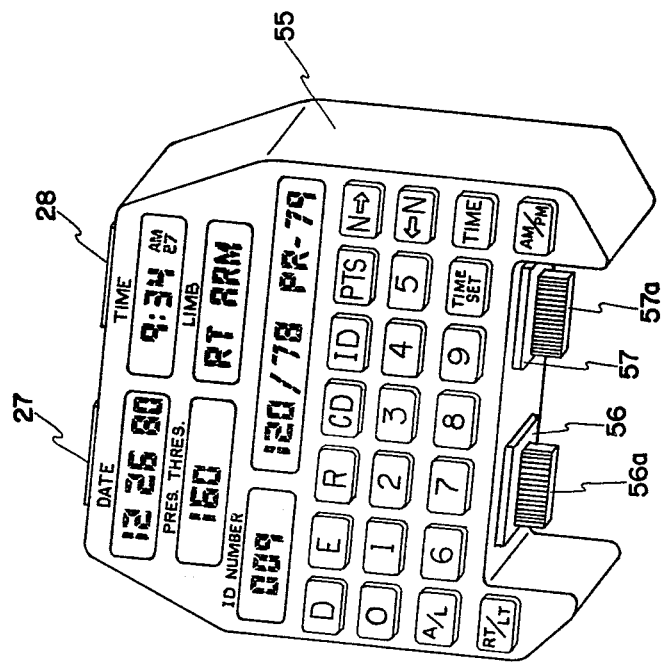

FIG. 12 is a perspective elevational view of an embodiment of the auxilliary unit that can directly be adapted to the embodiment of the device of FIG. 1 in order that said embodiment can function as a complete stepped-up advanced embodiment of the device of FIGS. 4, 5, and 6.

Figure 13:
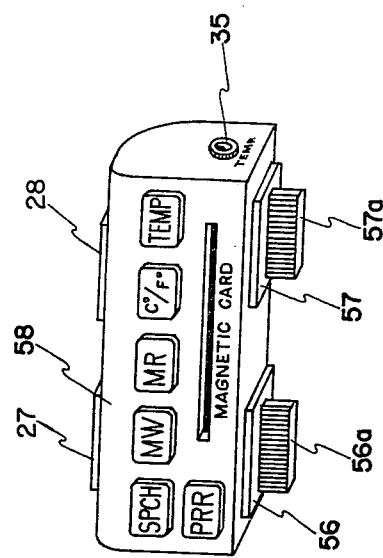

FIG. 13 is a perspective elevational view of a step-up embodiment of another auxilliary unit for adaptation with the embodiments of FIGS. 4, 5, and 6, to effect a coordinated functional efficiency of the advanced embodiment of FIGS. 8 and 8a. This auxilliary unit can also be adapted to auxilliary unit of FIG. 12 so that when both integrated auxilliary units are connected to the device of FIG. 1, the latter simpler embodiment can attain the functional capabilities of the device of FIG. 8.

Figure 14:
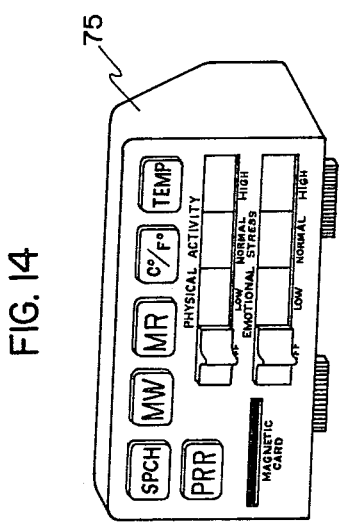

FIG. 14 is a perspective elevational view of another second step-up embodiment of an auxilliary unit for adaptation with both devices of FIGS. 4, 5, and 6, and which can also be interlinked with the auxilliary unit of FIG. 12 to effect a coordinated functional capability of the embodiment of FIG. 9.

Figure 15:
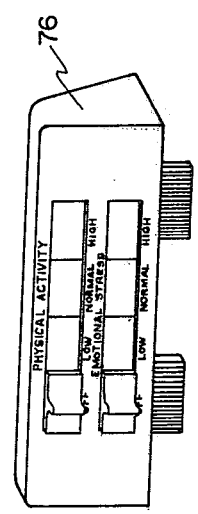

FIG. 15 is a perspective elevational view of another step-up auxilliary unit that can be linked with the step-up auxilliary unit of FIG. 13 to achieve the functional capabilities of FIG. 14, in order that the embodiment of the instrument shown in FIGS. 4, 5, and 6, can attain the functional capabilities of the device of FIG. 9.

Figure 16:
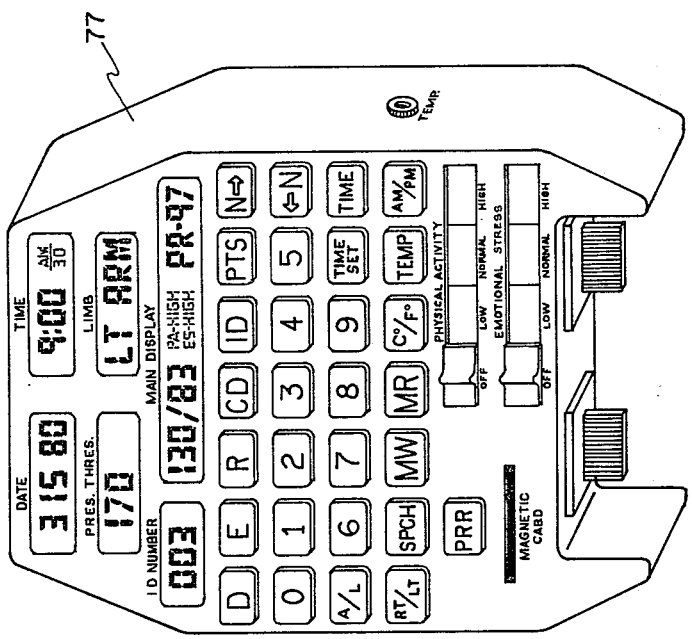

FIG. 16 is a perspective elevational view of an integrated auxilliary unit which can be interlinked electrically with the device of FIG. 1 to step-up toward the functional capabilities of the embodiment of FIG. 9.

Figure 2:
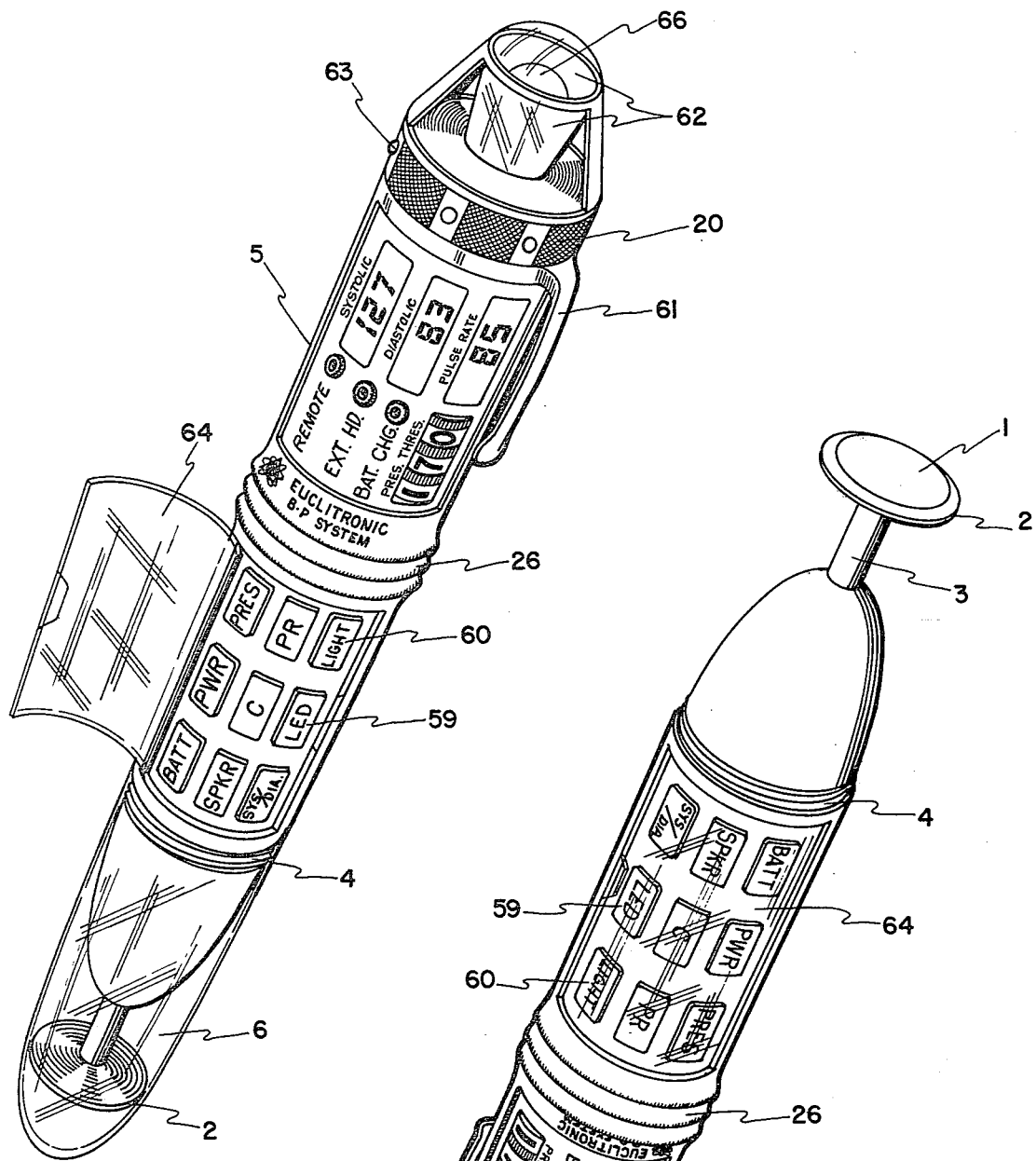
FIG. 2 is a perspective elevational view of an alternative embodiment of the invention without LED pressure display gauge, but with audio-visual signaling means coordinating with digital display of data. Incorporated in this device is a flashlight combination counterpart.
Figure 3:
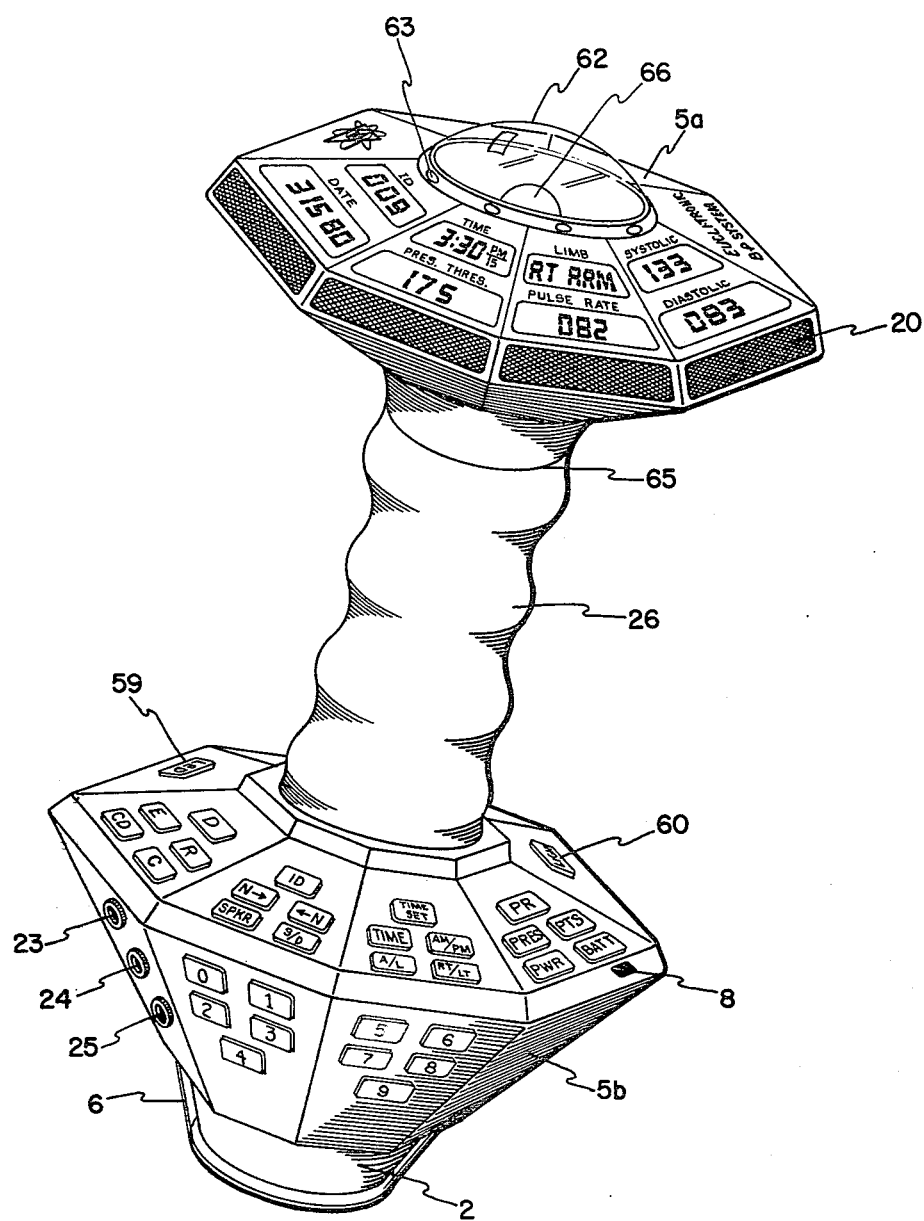
FIG. 3 is a perspective elevational view of another embodiment of the invention of special design with intermediary hand gripping portion.
Figure 17:
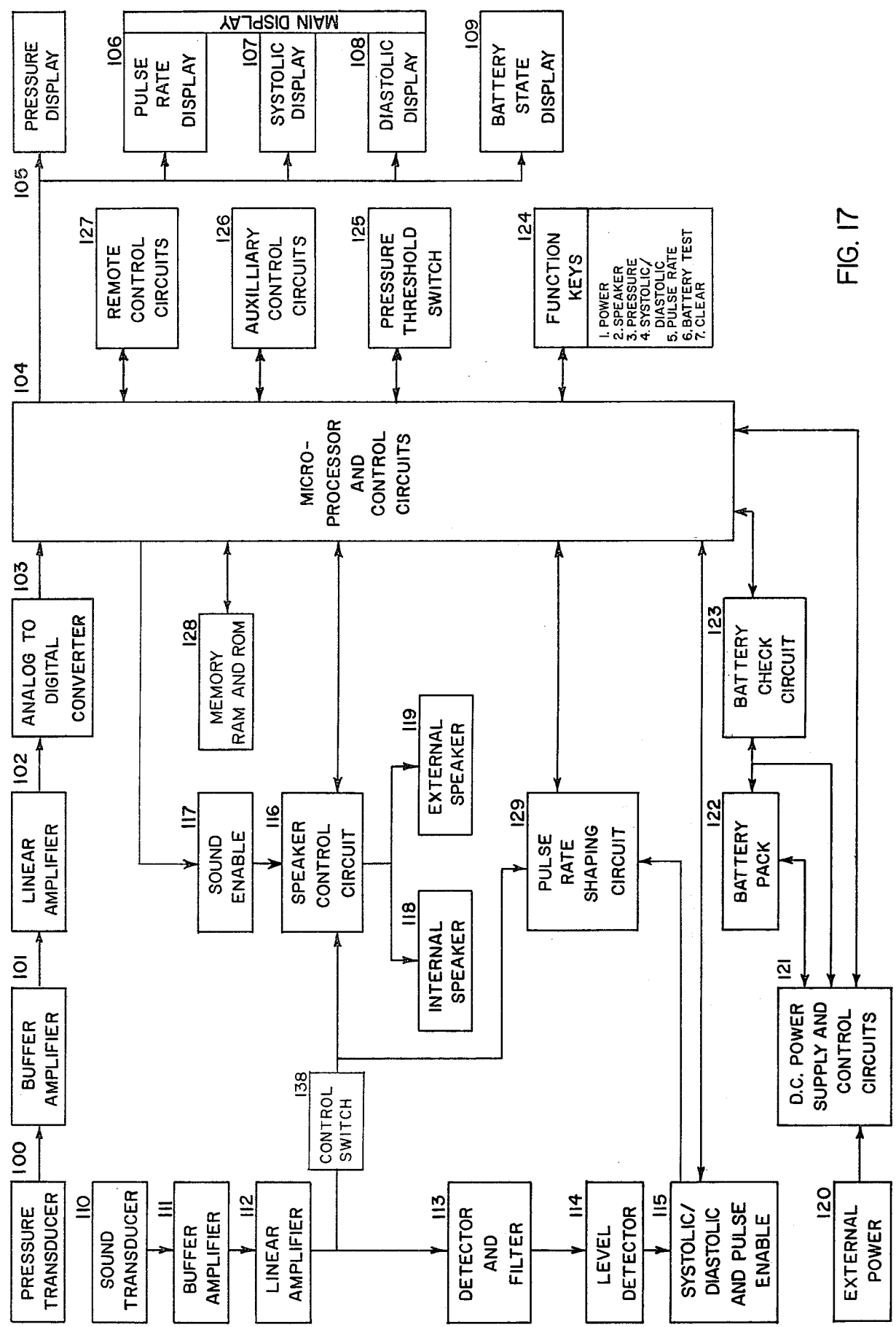

FIG. 17 is the electronic block diagram of the device of FIGS. 1, 2, and 3.

Figure 18:
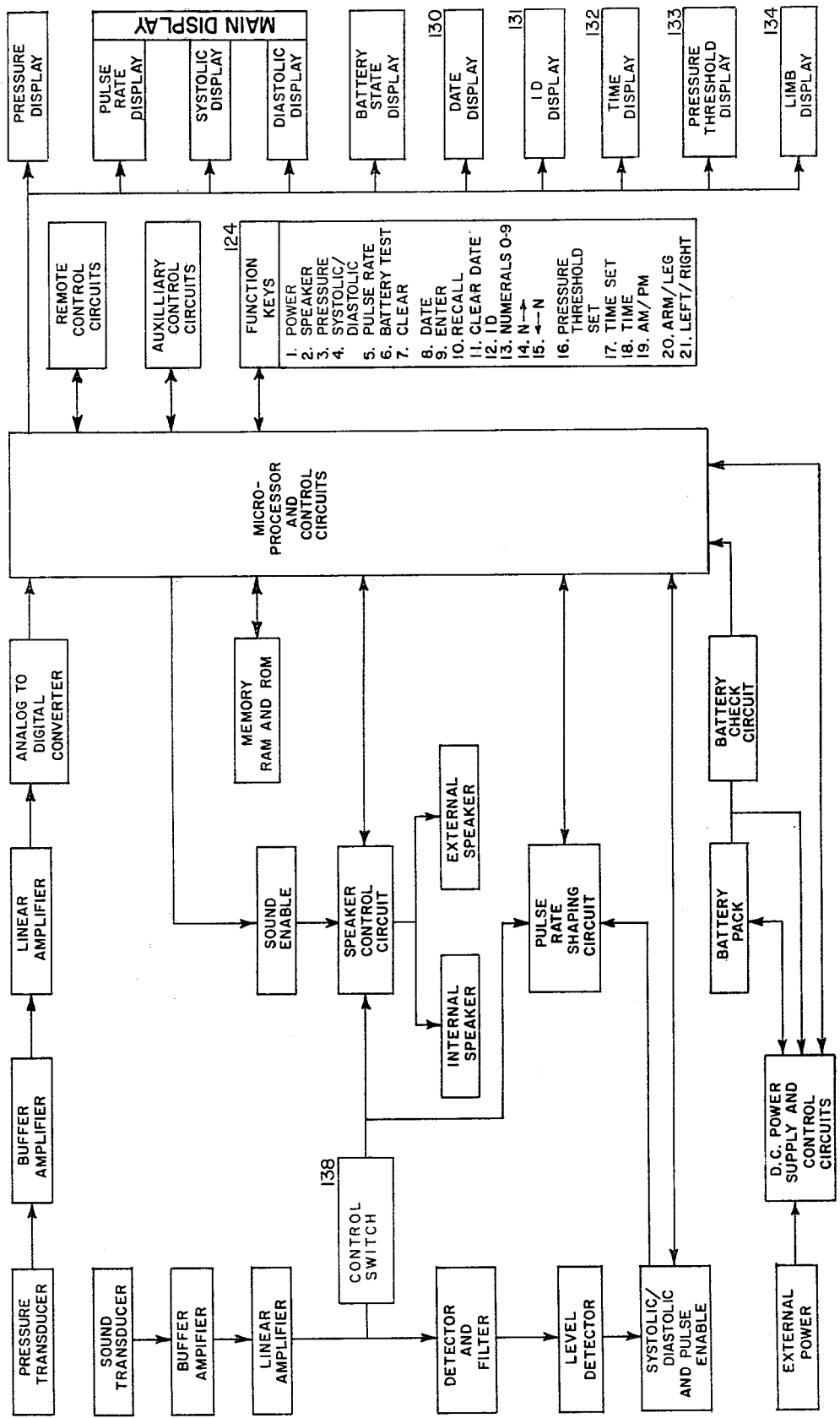

FIG. 18 is the electronic block diagram of the device of FIGS. 4, 5, and 6.

Figure 19:
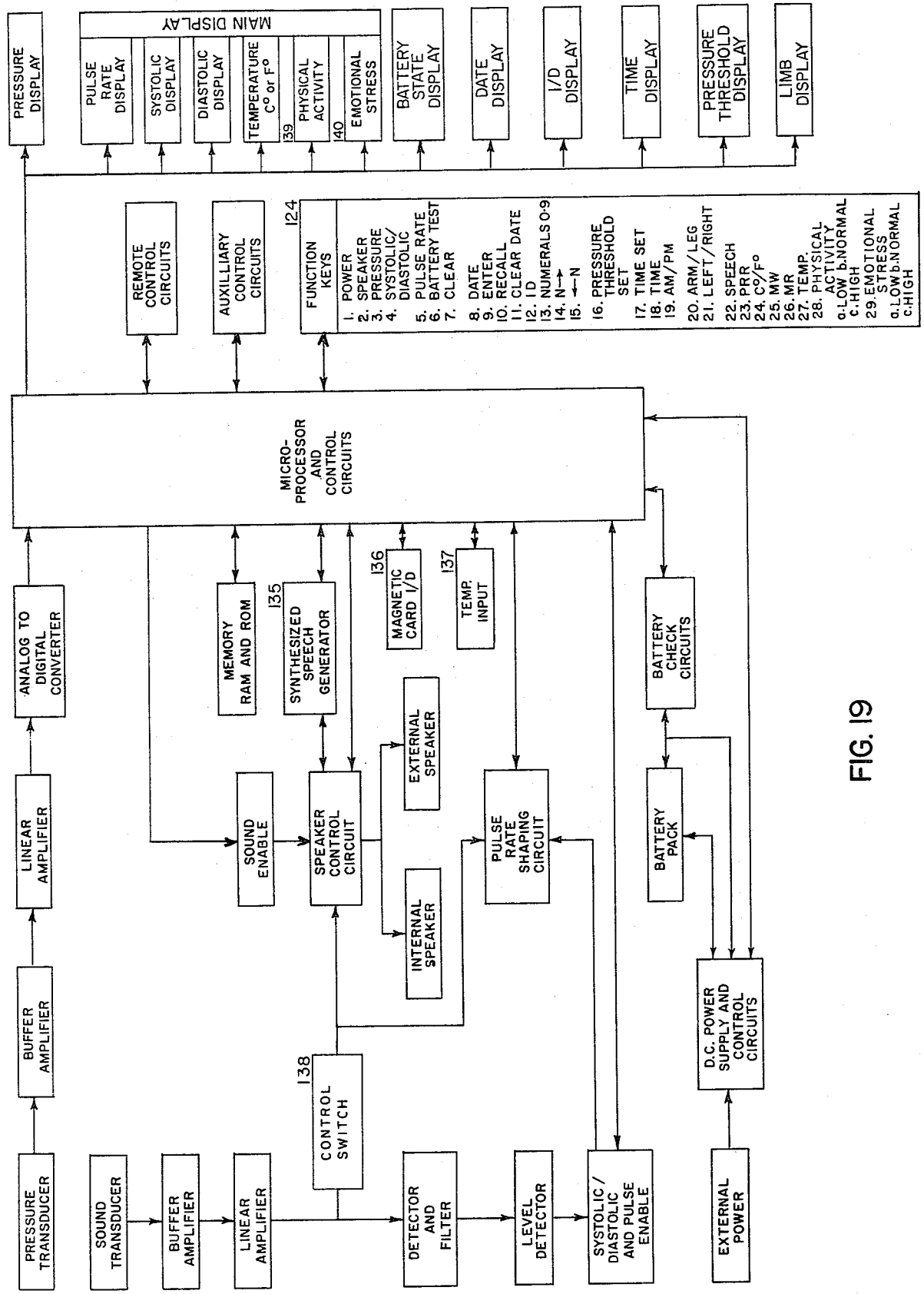

FIG. 19 is the electronic block diagram of the device of FIG. 9.

DETAILED DESCRIPTIONS

In general all the embodiments from FIGS. 1 to 9 are composed basically of a main body frame 5, pressure head applying means 2, acoustical transducer 1, occupying the central area of the pressure head applying means 2, a cover 6, that protects the said pressure head applying means, structural protrusions 27 and 28, for stronger interlinkage as the electrical sockets 27a and 28a, of a simpler embodiment become electrically coupled to the corresponding auxilliary unit through the edge connectors 56a and 57a of the said auxilliary unit, so that there will be a resultant stepped-up operational capability from the simpler embodiment to a more sophisticated type of the device.

In FIG. 1 is shown one basic preferred embodiment of the invention, having function key 13 which is labeled PR for pulse rate, 9 which is labeled PWR for power, 15 which is labeled CLR for clear, 7 which is labeled BAT for battery, 8 for battery check light, 11 which is labeled SYS/DIA for systolic and diastolic, 14 which is labeled PRES for pressure and 12 which is labeled SPKR for speaker. The system is activated by pushing or depressing the function key 9. When the device is connected through the home electrical outlet, the device gets its power from the available AC current. However, if the device is disconnected from the home electrical power, it operates on the buttery supply internally located in the device. In order to check for the optimal level of energy from the battery pack, the function key 7 which is a momentary off/on function key is depressed. After depressing the said function key 7, an adequate load is drawn from the battery pack while measuring the voltage and the current rate of change of the battery energy supply, during which time a continuous sound from 20 which is the speaker, is heard, and at the same time a continuous light from 8 appears which means that there is an adequate supply of energy coming from the batteries to operate the device in an optimal manner. However, if a beeping sound is heard through the speaker 20, and an intermittent light is generated or is seen at 8, these warnings indicate that the battery power is getting low and a replacement of the battery pack is essential in order to maintain optimal functional capabilities of the device. When the system is used primarily for determining only the pulse rate or the heart rate of the subjected individual, the function key PR as indicated by numeral 13 must be depressed and the system, especially the acoustical transducer portion 1 of the head applying means 2 is placed in contact with the radial artery or may be placed around the left portion of the chest where the heart sounds are dominant, so that as 1 detects the heartbeats which also corresponds with the pulse beats and during a certain period of time, a dynamic average pulse rate reading can be registered at the pulse rate register window 19. The pulse rate reading is an electronic calculation of the number of pulses per minute even through the actual period of time during measurement is not exactly one minute. When measuring the systolic and diastolic blood pressure readings, the function key 11 which is a permanent off/on button, must be depressed in the "ON" position in order to activate the system so as to properly latch the corresponding systolic and diastolic digital readings at the systolic register window 17, and the diastolic register window 18, respectively. The function key 14 which is a permanent off/on button for pressure, must be depressed in order that the LED pressure display gauge will be activated. When the pressure head applying means 2 is pushed against the upper arm at the bicep area where the brachial artery is located, the shaft 3 is pushed inwardly in an axial manner acting against the spring load 47 of FIG. 10, and displacing the Hall-effect transducer 49, generating a proportional voltage depending upon the compression degree exerted by the pressure head applying means 2 against the tissues over the brachial artery 54 of FIG. 11. The degree of pressure exerted against the tissues by the pressure head applying means 2 becomes translated to corresponding voltage levels which activates the microcomputer to demonstrate an analog representation of the pressure exerted at the LED pressure gauge 21. This analog representation is seen by the user as a traveling LED activation, either in an increasing or decreasing fashion, at the calibrated gauge. When the user of the device has familiarized himself or herself in the proper use of the pressure head applying means, by way of attaining an optimal degree of confidence in exerting the proper rate of compression and decompression procedure during blood pressure and pulse rate testing by watching the emitted light signals generated at pressure gauge 21, he or she may decide to turn off the function key 14 for pressure by quickly depressing function button 14 to return to its original undepressed "OFF" position, and then, entirely rely upon the registration of the corresponding systolic and diastolic digital readouts at 17 and 18, respectively. By shutting off function key 14, and not using the pressure gauge 21, the tester, will be able to conserve electrical energy. The LED or LCD pressure gauge 21 is covered by a transparent cover 22 which may have visual magnifying properties in order that the numerals 0 to 300 including the equidistantly positioned LEDs can easily be seen as larger images, thus achieving better visual aid for elderly individuals. When function keys 12 to 13 are depressed in the "ON" position, the system can be utilized for the audio-visual detection of both the heart and the pulse beats, thereby effecting an additional audible determination of whether or not the heart beats or the pulse beats are irregular or regular in occurrence, aside from achieving the dynamic digital readings of the heart rate or pulse rate per minute. The system can also be used in conjunction with the detection of the occurrence of the Korotkoff sounds, from the first phase of sound appearance to the fifth phase when the said Korotkoff sounds disappear during the concurrent determination of the systolic, diastolic, and pulse rate readings when operating the device under the pressure measuring mode. Another use of activating the speaker function key 12, is to be able to audibly hear the amplified unfiltered sounds of respiratory rales or other sounds of congestive nature that are evident in certain cases of respiratory infections, when the device is not in the pressure measuring mode. Therefore, the use of speaker 20 from where the amplified sounds emanate as activated by speaker function key 12 can be likened to a high powered stethoscope, but without connecting an ear piece to the listener's ear while attaining greater audio amplification. Function key 15 is a momentary off/on activation button for the purpose of clearing whatever digital displays for systolic at 17 and diastolic at 18, as well as pulse rate at 19, and including whatever latched lighted LED dots that may be displayed between the systolic and the diastolic range at the LED pressure gauge 21. There are two advantages of the LED pressure gauge 21: (1) It replaces the conventional mercury manometers which are quite fragile and requires a vertical standing position of the mercury column, and it also replaces the conventional aneroid pressure gauges that have many mechanical moving parts requiring frequent calibrations. The delicate metal needle pointer that pivots around in the conventional aneroid gauges is also eliminated. (2) It gives the system the electronic capability of an analog representation of the rate of compression and decompression exerted by the pressure head applying means upon the tissues immediately therearound the brachial artery, and, at the same time, it acts as a range locator between the approximate systolic and the diastolic readings because of the functional triggering and latching of the LEDs in a continuously lighted manner from the approximate systolic to the approximate diastolic levels at the LED pressure gauge 21, lasting only long enough to assure the optimal visual assessment and coordinative countercheck by the user in comparing the said approximate readings at the electronic LED pressure gauge to the more accurate latched digital readings for the systolic and diastolic registers at 17 and 18, respectively. The analog representation of the degrees of compression and decompression of the subjected tissues by the pressure head applying means 2 is an easier visual reference for the user on the rate of pressure change as compared to the visually confusing rate of change of digital readings.

The device is provided with a pressure threshold mechanical thumbwheel setter which is designated by numeral 10, and labeled "PRES. THRD.", the function of which is to enable the user to mechanically adjust the adequate pressure threshold at approximately the equivalence of thirty millimeters or more of mercury pressure higher than the subject's anticipated highest systolic blood pressure readings. The main advantage of setting the pressure threshold is to provide the device with the functional capability of activating relevant electronic circuitry through the microprocessor, only after the compression pressure upon the tissues therearound the brachial artery as applied by the pressure head applying means exceeds the set pressure threshold, when the device is operating in the pressure measuring mode, thereby resulting in conservation of electrical power. This embodiment as well as other preferred embodiments are provided with hand gripping portions 26 for easier handling of the device, and for optimal manipulation to effect better measurements of required data. FIG. 1 shows the cover 6 which is transparent, and in gripping engagement with the lower portion of the main body frame. There are three electrical sockets at the right side of the device which are also shown in FIG. 1a. These electrical sockets are: 23 which is for remote connection, 24 which is for connection with an external head phone when the user desires to hear the sounds more audibly without interfering with other people, or when using the device in an environment where there are undesirable noises such as in factories, or during travel, and, 25 which is for use with a battery charger that can be plugged directly to home electrical source. While the device is connected to the battery charger which is in turn connected to the home electrical source, the system does not use the electrical power of the battery. Instead, it is being operated by the current supplied by the said home electrical source as the battery is being recharged, as long as the "POWER" function key 9 is in the activated depressed "ON" position. FIG. 1a also shows the side view of the pressure head applying means 2 with the acoustical transducer portion 1, and the piston type axially displaceable shaft 3, all covered by plastic cover 6 in gripping engagement with the bottom portion 4 of the main body frame 5. The side view of the gripping portion 26 is shown for easy handling by the user. Also shown in the side view is the transparent cover 22, protecting the pressure display gauge. FIG. 1a also shows the right structural protrusion 28 that supports the corresponding right connecting structure of the adaptable auxiliary unit having electrical edge connectors. In FIG. 1b, which is the top view of the device of FIG. 1, the transparent cover of the pressure display gauge is also shown represented by numeral 22. The gripping portions 26 are also seen at both the left and the right sides. Structural protrusions 27 and 28 that accommodate the corresponding structures of the selected auxilliary unit are shown, as well as the electrical sockets 27a and 28a for electrically interlinking with the auxilliary edge connectors of the corresponding auxilliary unit.

In FIG. 2, there is shown another embodiment with a specially designed pen-like body frame having clip-on structure 61. All the other function keys in FIG. 1 are included, plus two more function keys added such as 59 which is the function key labeled "LED", and 60 which is the function key labeled "LIGHT". The LED function key is a permanent off/on function button which when depressed will activate the system to respond to the appearance of the pulses of the Korotkoff sounds so that the LED 63 situated therearound the upper section of the device will light concurrently with the occurrence of the first thudding Korotkoff sound, continuing to light intermittently, according to the appearances of the following Korotkoff sounds from phase 1 until phase 5, at which time, the diastolic blood pressure reading is latched at the diastolic digital display register. The LED also works in conjunction with the speaker system 20, so that each activation of the LED 63 will correspond to the occurrence of sounds emanating from the speaker 20, throughout the range from the first appearance of the Korotkoff sound until the muffling of sounds at phase 4 disappear. Both LED and sound activation will cease at phase 5. In this embodiment, the registers and digital displays for systolic, diastolic and pulse rate appear in a vertical manner as opposed to the horizontal arrangement of the same registers and digital displays as shown in FIG. 1. Similarly, the mechanical pressure threshold setter is also positioned in a vertical fashion, as compared to the mechanical thumbwheel setter which is positioned in a horizontal fashion as shown in FIG. 1. In this embodiment, the function keys which are also arranged in a vertical fashion can be protected by the transparent cover 64 with a hinge connection for attaining the opening and closing position. This cover protects the device from accidental activation or deactivation of the function keys while the device is in use. In this particular embodiment there is no LED pressure gauge that can measure or indicate the analog representation of the voltage that is directly proportional to the compression and decompression by the pressure head applying means 2 as seen in FIG. 1. The gripping portion 26 designed for better handling during the operation of the device is shown to be a three-fold corrugation therearound the central part of the device. Additionally, this preferred embodiment has an added feature—a flashlight system with electrical bulb 62 which can be activated to light when the function key 60 is depressed to attain the "ON" position. Therefore, this particular preferred embodiment can be used as a pen-light in addition to the functions already described in the preferred embodiment of FIG. 1, excepting the pressure display gauge 21. All the electrical sockets for REMOTE, EXTERNAL HEADPHONE and BATTERY CHARGE are also present as in FIG. 1, so that the functional capabilities of this preferred embodiment insofar as functioning with the aid of a battery pack or through the home AC electrical power, the use of the external headphone or the use of remote connections are the same as that of FIG. 1.

Figure 2A:
FIG. 2a is a perspective elevational view of the device of FIG. 2 illustrated in the inverted position and highlighting the pressure head applying means with built-in sound transducer.

In FIG. 2a is shown the inverted view of the same preferred embodiment shown in FIG. 2, but this time, the acoustical transducer area or portion 1 of the pressure head applying means 2 is better shown. The transparent cover that protects the pressure head applying means shown in FIG. 2, is a screw-on attachable and detachable plastic transparent cover. However, the cover is not shown in this FIG. 2a.

In FIG. 3, another embodiment is shown wherein the device is so designed so as to provide the appearance of a dumbbell configuration, wherein the gripping portion made for the proper placement of the hand during effective operation is situated between two octagonally shaped structures. The gripping portion 26 may contain the battery pack and other electronic elements. Between the upper octagonal counterpart of the device and the hand gripping portion 26 is a structural break 65 that runs in a circumferential manner. This structural break is a means of connecting and disconnecting the upper octagonal counterpart of the device from the rest of the lower hand gripping portion and the lower octagonally shaped counterpart of the device; the connecting means preferably being of a screw-on and off kind of interlinkage, so that, when the upper octagonal portion is disengaged from the rest, it is possible to replace used internally located batteries with new and powerful ones. The main difference between this embodiment from those described in FIGS. 1 and 2 is that, aside from the already described function keys shown in FIGS. 1 and 2, there are additional function keys. Function key marked "ID" when activated in the depressed "ON" position, will enable the user to enter the coded identification of the subject being tested. Another additional function key labeled "D" for date, is for the entry into the microcomputer's memory the adjusted actual data made possible by utilizing the proper combination of numbers selected from the function keys labeled 0 to 9. The real date can now proceed forward from the date of the actual setting. This works in coordination with the setting of the correct time once the function key labeled "TIME SET" has been activated in conjunction with the proper hour-minute-second setting into the microcomputer's memory with the aid of properly selected function keys ranging from 0 to 9. The function key AM/PM is a two-position function button, which when undepressed is in position to log into the memory unit the suffix AM, and when depressed, is in position to log into the memory unit the suffix PM, to correctly distinguish the AM from the PM in coordination with the proceeding hours, minutes and seconds according to the actual time set by the user in a specific geographical time zone. Function key labeled RT/LT, is also a two-way function button, which when undepressed is in position to log into the microcomputer's memory the abbreviation "RT" for right, and, which when depressed will be in position to log into the microcomputer's memory the abbreviation "LT" for left. Another two-way function button is function key A/L, which when in the undepressed state will be in position to log into the microcomputer's memory the word "ARM", and, when depressed will be in position to log into the microcomputer's memory the word "LEG". Therefore the combinations of function keys A/L and RT/LT, whether in the depressed or undepressed state, can enable the user to be able to enter into the microcomputer's memory such combinations as right arm or right leg or left arm or left leg, depending upon the limb location where the blood pressure measurement of the subject has been taken at a certain particular date and time. Function key labeled "PTS" for pressure threshold setting, when activated in the depressed "ON" position will be ready for the electronic logging of whatever pre-selected pressure theshold setting that may be optimal for a particular subject utilizing the desired combination of the function keys from 0 to 9. Ideally, the electronic pressure threshold setting can be set therearound 30 millimeters Hg. equivalence or more, above the anticipated highest systolic blood pressure reading of the subject at his or her worst circumstantial exposure. However, in the majority of cases a pressure threshold setting of about 200 millimeters of Hg. equivalence is more than adequate a setting for most subjects, except when one is known to have a major kind of hypertension, or if one is suspected of having a quite low systolic blood pressure. The reason for the use of the distinguishing combination for right arm, left arm, right leg and left leg is because of the possible inherent blood pressure differences in the readings in the respective areas because of the physio-anatomic makeup of the cardiovascular system, as well as in certain pathological conditions such as in coarctation of the aorta. It is important to remember that all of the aforementioned function keys, whether in the depressed or undepressed position in cases of the two-way function keys, or in the depressed "ON" position in cases of singular function keys, can only log in the corresponding data into the microcomputer's memory by the activation of each individual function key, followed by the activation of the function key labeled "E". This can be done by pressing the "E" function key which is a momentary on/off switch. The additional function keys are the following: (1) "TIME", which when depressed will enable the system to display the actual time at the respective digital display; (2) "D" for date, which when depressed will activate the system to display the actual date; (3) "CD" for clear date, when activated in the depressed "ON" position will enable the system to clear the date entered into the microcomputer in case of error in date entry during the current operation; (4) "R", when depressed in the "ON" position will enable the system to retrieve or recall the desired I.D. code number and the particular date by the use of the appropriate combination of function keys 0 to 9, so that the blood pressure and pulse rate data, and all other associated data will automatically appear at the corresponding digital display registers; (5) "N⟩", which when activated in the depressed "ON" position will automatically retrieve or recall the immediate next data from the date recalled according to the I.D. coding of a particular subject; said next data appearing in sequentially forward manner as long as the said "N⟩" function key is in the "ON" position. This "N⟩" function key may remain in the depressed "ON" position until undepressed as long as the user desires, in order that all other succeeding data can automatically appear in the same sequentially forward manner under a pre-programmed time frame (for example every 3 or 6 seconds) or whatever optimal time frame which may have been pre-programmed into the microcomputer to provide the user with an adequate time to visually assimilate the individual relevant sequence of data according to forward sequential time and date of previous measurements entered into the microcomputer's memory. This way the user will be properly informed of the data changes of the previous measurements done on a particular subject recalled within the desired time frame; (6) "⟨N", which when depressed to attain the "ON" position will automatically retrieve or recall all relevant data at the corresponding display registers according to the date and time and I.D. code of a particular subject, in a sequentially rearward fashion for the user's comparative data reference. The appearance of the relevant data in the respective display registers with respect to time and date can also be pre-programmed at a specific time frame for the adequate utility of the user. All these enumerated additional function keys are located therearound the upper sloped section of the lower octagonal portion of the device, and all the function keys labeled 0 to 9 are located at the lower conical face of the lower octagonal portion of the device. At the bottom of the octagonal portion of the device is shown the pressure head applying means 2 and the transparent cover 6. The variously labeled electrical connector sockets for remote, external headphone and battery charger are also located at the lower conical face of the lower octagonal portion of the device.

At the upper sloped section of the lower octagonal portion of the device is found the function key 59, which when depressed will activate the LED 63 to light during the appearance of the Korotkoff sounds, or to light during the sensing of the heart beats or pulse beats when the device has been activated by depressing the PR function key in the "ON" position. All the digital displays which are labeled: "I.D.", "TIME", "LIMB", "SYSTOLIC", "DIASTOLIC", "PULSE RATE", "PRES. THRES." for pressure threshold, and "DATE", are located at the upper sloped face of the upper octagonal portion of the device, and all have individual display registers according to their respective labels. At the outer sectors therearound the upper octagonal portion 5a of the device is shown 20, which is the speaker from which the sounds that are amplified emanate for the convenience of the user in order to optimally hear the audible amplifications of the Korotkoff sounds as well as the heartbeats or the pulsebeats depending upon the mode of operation. This embodiment can also be used as a replacement for the stethoscope with the additional advantage of having no earpiece, and providing the user with the optimal hearing of the amplified heart sounds which are helpful in the diagnosis of certain cardiac conditions. This also provides the user with the optimal hearing of the amplified respiratory sounds which are oftentimes essential in determining various respiratory conditions of the subject, especially during inflammatory reactions due to allergy or infection, or in diagnosing active asthmatic conditions. At the central portion of the upper octagonal portion of the device is shown the lighting system 62 which can be used as a flashlight when the function key 60 is depressed in the "ON" position, said function key 60 is located at the upper face of the lower octagonal portion 5b of the device. The battery check light 8 is located at the outer peripheral of the lower octagonal portion. The main advantage of this kind of dual octagonal configuration with the intermediary hand-gripping portion is the capability for greater control during the operation of the device, plus its structural value in that the device can be laid on a flat surface without danger of its rolling over on account of the inherent cooperating symmetry and parallelism of the corresponding pair of lower and upper octagonal borders of the upper and lower octagonal portions of the device. This preferred embodiment, however, is similar in one way to the embodiment of FIG. 2 in the sence that there is no analog LED pressure display gauge, a feature which is present in the embodiment of FIG. 1. The main difference between this embodiment and the embodiments of 1 and 2 is that, aside from its having an electronically adjustable setting of the pressure threshold as opposed to the mechanical thumbwheel pressure threshold settings of embodiments of FIGS. 1 and 2, it has the additional relevant aforesaid function keys to attain the said electronic pressure threshold setting, including the corresponding digital display registers that are not present in both the embodiments of FIGS. 1 and 2. Additionally this has the capability of entering and recalling all desired data to and from the microcomputer's memory system for the convenience of the user.

In FIG. 4 is shown another alternative embodiment of the device wherein all the function keys of the embodiment of FIG. 3 are all included and situated at the front face of the device designated by numeral 34 inclusively, extending from broken lines a to b. The difference between this embodiment as compared to the embodiment of FIG. 3 in that this particular embodiment has an analog LED pressure gauge 21 which is illustrated in a wrap-around pattern and having been calibrated from 0 to 300 surrounding the speaker 20. Another difference here is the presence of a main register designated for the digital readouts for the systolic, diastolic and the pulse rate per minute, instead of the separated digital display windows as shown in FIG. 3. All the other singular displays for digital data such as "I.D. NUMBER", "DATE", "TIME", "PRESSURE THRESHOLD", and "LIMB", are the same as that of FIG. 3. Yet another difference in this embodiment is the presence of the structural protrusions 27 and 28 with the corresponding electrical socket connectors for coupling with the respective auxilliary unit, compared to their absence in the embodiment of FIG. 3. Still another difference here is the configuration of the pressure head applying means which is arc-like in shape, at the lower portion of which is found the acoustical transducer. The reason for this arc-like shape is for optimal adaptation against the convex configuration of the bicep portion of the upper arm to effect an optimally tight and adequate engagement in the process of compression and decompression of the brachial artery during the measurement of the systolic and diastolic blood pressures as well as the pulse rate per minute of the tested individual. This design of the pressure head applying means, like the other designs of the same pressure head applying means, will substantially, easily justify the replacement of the arm-cuff which is quite time-consuming and error-prone. This is because of the rationale that, after all, the detection of the Korotkoff sounds is merely based on the adequate compression and the easy decompression of the arterial vessel such as the brachial artery. The arm cuff's total circumferential compression of the upper arm is not really that important when one investigates the case in a deeper analytical point-of-view, due to the fact that the compression of the bottom portion of the arm does not really achieve an actual direct compression of the brachial artery, but only contributes in compressing the said brachial artery because of the pull of the non-elastic outer portion of the arm-cuff as the internal bladder portion is pneumatically inflated. Therefore, by substituting the properly calibrated pressure head applying means with an excellent factory calibrated spring load corresponding to the acceptable optimal pressure equivalence as expressed in millimeters of mercury, the utility of the compression arm-cuff can become obsolete. Also, the user of this new invention will be able to achieve a faster and more reliable measurement of the blood pressure and pulse rate data without experiencing the disadvantages of the old fashion, yet currently used, Riva-Rocci arm-cuff. The cover 6 is shown disengaged from its protective position from the lower end of the device. The instruction, "DEPRESS AND RELEASE SLOWLY", with an arrow pointed downwards, gives excellent instructions to the user for the proper manipulation of the device during the execution of the optimal and comfortable rate of compression and decompression of the upper arm, using the pressure head applying means 2. The rate of compression and decompression of the upper arm can be controlled by the user with little practice in order to give a smooth rate of analog visual representation at the LED pressure gauge being activated to the corresponding levels proportional to the degree of voltage generated secondary to the displacement of the Hall-effect transducer of the pressure head applying means as the tissues therearound the targeted arterial vessel is subjected to compression and decompression. During the blood pressure and pulse rate detection mode effected by the activation of the S/D function key, the microcomputer detects and enables the first Korotkoff sound only after the pressure threshold setting which was previously adjusted has been exceeded by the compression pressure exerted by the pressure head applying means. This procedure can properly be executed by watching the ascending activation of the individual LEDs at the pressure gauge passing the point of the pressure threshold setting. For conservation of electrical energy, the LED pressure gauge can be inactivated by turning off the function key labeled "PRES" (for pressure) after the user gains adequate experience and technique in the proper compression and decompression of the pressure head applying means against the area of measurement. He can then feel confident by just relying on the digital readings at the proper systolic and diastolic display registers. As soon as the activation of the microcomputer for the detection and enabling of the systolic and diastolic pressures including the pulse rate have been triggered after passing the level of the set pressure threshold, the acoustical transducer 1 located at the underside of the pressure head applying means 2 will start to detect for the first appearance of the Korotkoff sound, then amplifies the said sound as soon as it occurs and concurrently latches the corresponding systolic digital data at the systolic digital display register. As the Korotkoff sounds continue, the digital displays at the diastolic display register becomes enabled, proceeding in digital decrements until the diastolic level has been reached, at which instant the diastolic data get latched at the diastolic digital display register. When the LED pressure gauge is activated by depressing the "PRES" function key on the "ON" position, the corresponding LED at that point or nearest that point of systolic blood pressure detection, becomes latched, and the succeeding LEDs downwards also became latched in a continuous lighted manner, describing a train of latched lighted LEDs as long as the Korotkoff sounds continue to occur until the Korotkoff sounds disappear. The latched LEDs, from the first detection of the Korotkoff sound to the disappearance of the said Korotkoff sounds provide a visual means that can be likened to a range locator, for the benefit of the user in providing him with an approximate range between the systolic and the diastolic blood pressure levels. The latched LEDs can stay in the continuously lighted manner for several seconds and will automatically fade out, or they may be cleared immediately by depressing the function key marked "C" for clear, or else they may be deactivated at the moment the user begins another pressure measuring cycle.

The systolic as well as the diastolic readings including the pulse rate data are digitally displayed at the main register 33. The other data for the "I.D. NUMBER", "DATE", "TIME", "PRESSURE THRESHOLD" and "LIMB" including the data for the main register 33 will be visibly displayed until such data is entered into the microcomputer's memory by depressing the function key labeled "E", or by depressing the function key labeled "C" in case all the displayed data is to be cancelled.

As soon as the user starts another measuring cycle for the systolic, diastolic, and pulse rate, by first reactivating the compression procedure of the pressure head applying means 2, the set of systolic, diastolic and pulse rate data which have just been registered will automatically be cancelled, while the other data in the independent display registers 29, 30, 31, and 16 can still remain. This embodiment has also a battery check light 8 which can be activated by depressing the function key labeled "BATT." A continuous light seen at 8, and a continuous sound heard through the speaker 20, signify that the electrical power of the battery is still adequate for optimal operation. However, if the battery check light 8 intermittently lights up, and a beeping sound is heard from speaker 20, the battery's electrical power is getting low, thus emphasizing the need for a new set of batteries or the need for immediate proper battery recharging by connecting the device to a battery charger that can be directly connected to commercial electrical power source through electrical socket 25. In this way, the device can function adequately as the batteries are being recharged by the battery charger that is connected to the commercial power source. As in the other embodiments in FIGS. 1, 2, and 3, there is also provided the electrical sockets 23 designated for remote, and 24 designated for external headphone. The hand gripping portion 26 is shown in the right hand gripping engagement preparatory for use.

In FIG. 5 is shown another configuration of the preferred embodiment having all of the same elements of FIG. 4, but of a different structural shape. The only difference between this embodiment and that of FIG. 4 is the vertical and straight layout of the LED pressure display gauge ranging from 0 to 300 mm. Hg. equivalence, instead of a wrap-around LED display gauge pattern as seen in FIG. 4. The speaker 20 is located between the set of displays for the digital readouts at 29, 30, 31, 16, 32, and 33, and the set of function keys designated by numeral 34, inclusively from broken lines "a" to "b".

All of the function keys and all of the display registers in this embodiment are the same as that of FIG. 4. Structural protrusions 27 and 28 are also present here as in FIG. 4. The pressure head applying means is shown to be arc-like in configuration, and at its lower underside is the acoustical transducer 1. Again, the reason for this arc-like shape is for better form fitting engagement against the convex anatomical makeup of the upper arm and for better effecitivity in attaining the proper occlusion and deocclusion of the brachial artery and for attaining greater sensitivity in the detection of the Korotkoff sounds. The axially displaceable piston 3 is shown providing structural tolerance for the pressure head applying means 2 to be able to attain maximum compression and decompression of the said brachial artery. The main frame 5 narrows down at the lower section providing a hand gripping section to accommodate the hand of the user, for the excellent self-application of the device. The cover 6 is shown in section and in covering engaging relationship with the device to protect the pressure head applying means as well as the acoustical transducer. The hand gripping portions 26 are found in both sides for better hand-gripping use. FIG. 6 is the left side elevational view of FIG. 5 showing the side views of the main display register 33, the function keys 34 and the structural protrusion 28. The electrical sockets 23 for remote, 24 for external headphone, and 25 for the battery charger are all clearly shown. The gripping portion 26 is also shown with straight grooves for achieving greater gripping capability for the proper handling of the device. The side view of 4 which is the lower portion of the device, the piston 3, the head applying means 2, and the engaged cover 6 in section are also shown.

FIG. 7 is the preferred embodiment of the instant device especially for use in doctor's offices, clinics, laboratories and hospitals, or for home and office use by one individual for application to others. There are shown all the various independent digital displays for "I.D. NUMBER", "DATE", "TIME", "PRESSURE THRESHOLD", and "LIMB". The main display 33 is not only used for the correct display of both the systolic and diastolic blood pressure and pulse rate data, but also used for displaying the temperature expresed in degrees of centigrade or fahrenheit, once a corresponding temperature probe has been properly attached to the temperature electrical socket 35 located at the side of the device, and while the said temperature probe is in proper placement with the right body location of the subject. Although the preferred embodiment illustrates a blood pressure reading of 150 over 102 for the systolic and the diastolic values, respectively, and the pulse rate data is illustrated with a value of 112 per minute, it is to be emphasized that, in this same main display the temperature of the subject, expressed in degrees of fahrenheit or centigrade can also be registered during the temperature measuring mode of the device. Likewise, the temperature data can also be entered into the microcomputer's memory based upon the date, time, and I.D. number of the subject for future data retrieval. Moreover, it is also to be clarified that the length and the width of the main digital display register 33 is only arbitrary in this design, so that both width and length of the said display register may be increased in dimension so as to accommodate not only the systolic and diastolic blood pressure and the pulse rate readings, but also the temperature of the subject in the same time frame before data entry into the microcomputer's memory. Therefore, the abovementioned data can be retrieved concurrently in the same main display register at a later time of data recall. In this embodiment it can be seen that there is another electrical socket connector for temperature labeled "TEMP" represented by numeral 35, in addition to the electrical sockets 23, 24, and 25, which have already been previously described and illustrated in the aforementioned previous embodiments. As far as the function keys are concerned, there are two additional keys included, such as a function key for temperature labeled "TEMP", and a function key for centigrade and fahrenheit, both expressed in degrees labeled "C.°/F.°", which is a two-way function button. To operate the device for the temperature measurement of the subject, the function key labeled "TEMP" must be activated by depressing the said function key is the "ON" position so that the system can coordinate with the temperature probe attached to the electrical socket connector 35, as the said temperature probe is placed at certain selected parts of the subject, such as under the tongue or placed intra-rectally. When the function key "C.°/F.°" is in the undepressed position, the device automaticaly measures the subject's temperature in degrees centigrade and displays the value at the main register 33, however, when the same function key is depressed, the subject's temperture is calculated in degrees fahrenheit, displaying the data at 33. The specially designed hand gripping portion 36 is for the optimal use of one individual to another, to effect the proper engagement of the pressure head applying means 2, with its acoustical transducer portion 1 placed against the brachial artery. The compression and decompression action of the pressure head applying means 2 can be done slowly but efficiently, maintaining a rate of smoothly moving lighting activation at the analog LED pressure gauge. Note that the various markings in the function keys are so placed in a manner that can easily be readable and distinguishable by the user. The same is true with the various labels of the different electrical sockets and the digital display registers, but excluding the main register 33 which is not labeled. All the other data in the various display registers are shown at an optimally placed angle. The centrally located speaker is surrounded by a rectangularly arranged LED pressure analog display gauge, having calibrations from 0 to 300 which are interspaced equally; between each LED is a calibrated value equivalent to 5 mm. of Hg. This is consistent with all the embodiments having the LED pressure display gauge with the exception of the embodiment of FIG. 8 wherein the value between each LED is equal to a calibration of 2 mm. of Hg. equivalence. The function of this electronic analog pressure gauge is similar to those already described in the previous embodiment. The markings "DEPRESS AND RELEASE SLOWLY" with its corresponding arrow pointed toward the central part of the pressure head applying means 2 is also illustrated. All the function keys in this embodiment are represented by numeral 34 inclusively from dotted lines "a" to dotted lines "b". At the digital display register for "ID NUMBER" is a sample of a patient coded with number "007". This will distinguish this patient from any other individual for proper identification during the correct data entry and future data retrieval of the relevant data measured based on the respective date and time of measurement, including the set electronic pressure threshold of 190 mm. of Hg. equivalence used, and the limb location where the measurement was made, which in this case is shown to be at the right arm. When recalling all relevant data previously entered into the microcomputer's memory, the earliest actual time of a specific date recalled will first appear with the respective data registered at the various displays, before proceeding towards the latest actual time of that same date in cases wherein a plurality of measurements have been performed during that said date, as the function key marked "N▷" is activated. If there was only one measurement done during that particular date recalled, the next set of data relevant to the same patient, according to the next forward sequence of time and date of measurements performed, appear at the various displays when the same function key "N▷" continues to be activated. This sequentially forward process is achieved automatically with one set of data appearing in consecutive order within a certain pre-programmed time frame. When recalling the data of a certain patient such as the one having an I.D. number "007", based on a specific date recalled, the reverse happens when the user activates the function key marked "◁N" which means next rearwards. In this case, all relevant data displayed in the next rearward order are the ones corresponding to the latest time of the next date backwards, and then proceeding to the earliest time of that date if there were several measurements done and entered during the said next rearward date, before proceeding to the next rearward set of data of the next date going backwards. This operation will continue in a sequentially backward fashion as long as the function key "◁N" is activated. A period of about every 3 to 6 seconds should be a sufficient time frame for displaying one set of data before proceeding to the next set of forward or backward data as the user activates the "N▷" or "◁N", respectively. The hand gripping portion 36 may contain additional battery supplies for future use as a reserve in case the main batteries should run low in electrical energy; both sets of batteries are located inside the main framework. This device can be used as a portable unit using batteries, or it can be connected to a commercial electrical power for operating the device while the batteries are in the process of being recharged. This embodiment may also be provided with an automatic electrical link between the main battery pack and the circuitry of an auxilliary battery pack in order that the device can have the capabilities for additional automatic electrical energy supply from both battery packs to maintain the required electrical power for the proper operation of the device, and, at the same time ensuring the microcomputer's memory unit with a stand-by adequate electrical energy supply so that all relevant entered data will not be cancelled during the process of battery replacement.

FIG. 8 illustrates some other function keys for speech labeled "SPCH", memory write labeled "MW", memory read labeled "MR" and pulse rate rhythm labeled "PRR" as additional features to those embodiments already described.

The "PRR" function key, when activated will register the information on the regularity or irregularity of the pulse rate at the main register within a certain preset time frame. The information registered may include the dynamic pulse rate value plus the computer analysis of "regular" or "irregular" seen beside it. This measuring mode can be independent from the Pulse Rate mode and the Systolic/Diastolic pressure measuring mode of the device and can be entered into the microcomputer's memory and independently retrieved at a later date. In this manner, the "PRR" function can override the "PR" mode. However, the device can also be designed so that the "PRR" mode can work in conjunction with either or both the "PR" and the Systolic/Diastolic pressure measuring mode and then concurrently displayed in the various displays accordingly. There is also a magnetic card slot 37 for the insertion of the magnetic card both for writing data into the card and the reading of data from the card, depending upon the I.D. number and other relevant information. The added function keys including the magnetic card entry slot 37 are inclusively represented by numeral and letter combination 34a from broken lines "c" to "d". All the other function keys found at the upper portion of the device are inclusively represented by numeral 34 from broken lines "a" to "b". The main register 33 is shown with a reading of 110 (systolic pressure) over 80 (diastolic pressure), and a pulse rate reading of 84 per minute. For example, in the various digital display registers for I.D., DATE, TIME, LIMB, and PRESSURE THRESHOLD, are shown having the following data: The I.D. code for a subject is 003; the date if 12/26/80; the time is 9:39 and 26 seconds p.m.; the measurement done at the left arm; and the used pressure threshold of 150 expressed in millimeters of mercury equivalence. Like the other embodiments, this also has the upper external protrusions 27 and 28 for a stronger structural mating with the appropriate auxillary unit to step-up this device to a more advanced embodiment with proper interlinking edge and socket electrical connectors. The embodiment also illustrates an incomplete quadri-angular pattern of LED pressure gauge 21 shown in equally interspaced increments of 2. mm. of Hg. equivalence from 0 to 300. Surrounded by this LED pressure gauge is the speaker 20 with decorative sun-like design surrounding the said speaker. Also shown are the left and right hand gripping portions 26 and the engaged transparent cover 6 shown in section, protecting the head applying means 2 and the acoustical transducer portion 1.

FIG. 8a shows the side elevational view of the same embodiment of FIG. 8 illustrating the side-view of the main body frame 5, the hand gripping portion 26, the lower section 4 of the device accommodating the axially displaceable pressure head applying means 2, and the engaged transparent cover 6 shown in section. At the upper part of the device are the electrical sockets 23, 24, 25, and 35 as have been illustrated in the embodiment of FIG. 7. The structural protrusion 28 shown in side view can also be seen.

In FIG. 9, the face of upper segment 5a contains the digital display registers including some function keys labeled "SPCH", "MW", "MR", "C.°/F.°", "TEMP" and "PRR" represented by 34a from broken lines "c" to "d", and a magnetic card entry slot. At the left side portion of the same segment is found the electrical connector sockets. The speaker is found at the top portion of the device. At the face of the lower segment 5b are found all the other function keys including two additional slideable function keys such as 67, which is for logging into the device's memory the level of physical activity, and 71 which is for logging into the device's memory, the level of emotional stress; both 67 and 71 will have the level delineation of "LOW", "NORMAL" and "HIGH" so that the tested individual can have these level distinctions for both the physical activity and the emotional stress conditions, he or she is under during the tme of data measurement. The function keys 67 and 71 can both be slid to the proper positions indicated by the respective markings such as; 68 for "LOW", 69 for "NORMAL", 70 for "HIGH" as far as physical activity is concerned; 72 for "LOW", 73 for "NORMAL" and 74 for "HIGH" in accordance with the emotional stress of the tested individual. At the lowermost section of the same segment is found the pressure head applying means 2 plus the acoustical sensor 1. The cover is shown detached from the main body. All the other functions are similar to the embodiment of FIG. 8.

FIG. 10 illustrates the internal framework of the invention exposing in section the lower portion of the main body framework 5, with the centrally located pressure head applying means 2 protruding externally and downwardly, and, continuing upwardly with a piston-like structure, also shown in section; directly opposing against the uppermost portion of the said piston framework is a factory calibrated spring load 47. Embedded at the lowermost central portion of the pressure head applying means is the acoustical transducer 1, having wiring 39 embedded centrally inside the piston-like structure 3; said electrical wiring 39 comes out of the piston-like structure and held in place by wire connector 40, then proceeding upwards in electrical wiring conduction continuity to interconnect with wire connector 41 before proceeding with further connections to the proper electronic circuits. The piston-like structure 3 has a lateral structural protrusion 43 that runs circumferentially in an equal manner, so as to have its lower edge in the proper equally engaging relationship with 42, which is the corresponding engageable structure that restrains the farther outward movement of the piston and the pressure head applying means. The upper portion of the piston-like structure located higher than structural protrusion 43 is the continuity of the piston-like structure now designated as 44, also shown in section, and, at the uppermost portion of 44 is structural protrusion 46 acting as a vertical guide for the spring load 47. At the right side of 44 and at the lower part of its corresponding structural mating protrusion 45 of the internal body framework, is found the pair of cooperating components of the Hall-effect transducer 49 which senses the displacement from the basal 0 displacement, and transmitting the linear voltage signals proportional to the degree of displacement resulting from the compression and the decompression activity of the pressure head applying means and resulting in the registration of the calculated relevant data to the respective analog and digital displays. From the Hall-effect transducer is electrical wiring 51 connected and placed in position by electrical connectors 50 and 52. The load of the spring 47 is factory calibrated, and the adjustment can be made by adjusting the screw adjuster 48 shown directly interacting against top of the uppermost section of the spring 47. The preferred factory spring load, in directly axial opposition to the piston-like structures 3 and 44, is based on 0 displacement of the pressure head applying means. Any substantial displacement of the head applying means 2 and the corresponding displacement of the piston-like structures 3 and 44 against the spring 47 that goes in an upward axial displacement fashion, causing a relative displacement of the interacting previously aligned Hall-effect transducer components, will be translated into proportional voltage signals visually shown at the analog LED pressure gauge. The lower portion of the main body frame work is designated by numeral 4 which allows proper engagement for the attachment of the cover.

FIG. 11 shows the left arm with the brachial artery 54 represented by broken lines, and, illustrated as being compressed slowly by the head applying means of the device of FIG. 4. This Figure demonstrates how easily the device can be handled by the right hand to attain the proper compression and the gradual decompression of the upper arm, thereby effecting an easy means of extravascular occlusion of blood flow through the brachial artery, then followed by a gradual decompression of the area by gradually releasing the pressure exerted by the pressure head applying means, for data measurement of both the systolic and the diastolic readings sensing for the Korotkoff sounds generated by the turbulence of the flowing blood at the critical level of the gradually opening brachial artery. The pulse rate during this process, can also be concurrently measured because the Korotkoff sounds, from the first phase to the fifth phase will be detected wth each cardiac cycle during the time frame from phase 1 to phase 5. The calculator's microcomputer can give a dynamic digital reading of the pulse rate estimated per minute even though the actual measurement time is not exactly a one-minute period. As can be seen in this Figure, the arch-like configuration of the lower portion of the pressure head applying means optimally engages with the convexity of the upper arm over the section of the brachial artery, and, since the system does not involve a wrap-around compression cuff, it is faster to operate, less painful to the patient and does not impede the venous circulatory return of blood to the heart. For example, in this case, the calculator shows a patient having a designated I.D. number of "007", having a date of Mar. 12, 1980, an actual time of 7:20 and 30 seconds p.m., a pressure threshold set at 170 mm. of Hg. equivalence, the left arm signifying the limb location where the blood pressure of 125/83 and the concurrent pulse rate reading of 078 per minute, have been made. If the user desires to log into the device's microcomputer's memory, all current data, he simply depresses the function key marked "E", so that the said data can again be retrieved or recalled from the microcomputer's memory at a later date.

In FIG. 12 is shown an auxilliary unit illustrated in perspective view; said auxilliary unit can be adaptable for electrical connection with the proper electrical socket connector of the embodiment of FIG. 1, in order to advance the said embodiment to the preferred embodiment of FIG. 4. As can be seen, the auxilliary unit contains all the other function keys not present in FIG. 1, and also contains the other digital display registers for "DATE", "TIME", and "PRESSURE THRESHOLD"; the said pressure threshold in this case is electronically set, rather than mechanically set as in FIG. 1. Additional display registers are for the "LIMB", "I.D. NUMBER", and the "MAIN REGISTER" for both the systolic and diastolic data as well as for the pulse rate readings. The auxilliary unit, when connected to the embodiment of FIG. 1, electronically integrates the two to act as a single functional unit thereby attaining the entire operational capabilities of the embodiments of FIGS. 4 and 5. The electrical connectors shown in this drawing are 56a and 57a, which are standard edge connectors with the appropriate number of electrical connections to fit into the electrical sockets 27a and 28a of FIG. 1b which is the top view of the preferred embodiment of FIG. 1. For stability, the auxilliary unit has plastic structural protrusion 56 and 57 to engage in optimal mating relationship with 27 and 28 of FIGS. 1 and 1b.

In FIG. 13 is shown another embodiment for an auxilliary unit which can be adaptable to the embodiment of FIGS. 4 and 5 in order to achieve the functional capabilities of the embodiment of FIG. 8, which is another more advanced model. As illustrated, the auxilliary unit has other function keys for speech, memory write, memory read, centigrade and fahrenheit, expressed in degrees, temperature and pulse rate rhythm, plus a magnetic card entry and retrieval slot. It also shows 35 which is the electrical connector for temperature. Also shown are electrical edge connector prongs 56a and 57a with the appropriate number of electrical connections that can mate in a proper fashion with the electrical sockets of the embodiments of FIG. 4 and FIG. 5 to attain the operational capabilities of the embodiment of FIG. 8. This auxilliary unit can also be adapted to be electronically connected with the electrical socket connector of auxilliary unit of FIG. 12, so that when the auxilliary unit of FIG. 12 becomes coupled to the embodiment of FIG. 1, the additional auxilliary unit of FIG. 13 can enable the embodiment of FIG. 1 to step-up in the operational capabilities of the device of the embodiment of FIG. 8, altogether operating in a single unit.

It is to be emphasized that when the auxilliary unit of FIG. 12 is properly linked with the embodiment of FIG. 2, the device will have the capability of an electronically set pressure threshold which overrides the mechanical thumbwheel pressure threshold setter of the embodiment of FIG. 1.

FIG. 14 is another embodiment of an auxilliary unit which can be adapted only to the auxilliary unit of FIG. 12 to step-up the functional capabilities of the simpler device of FIG. 1 to attain integrated operational functions equal to that of the advanced embodiment of FIG. 9, which has been previously described.

FIG. 15 is yet another embodiment of an auxilliary unit which can only be adopted to the auxilliary unit of FIG. 13 to attain an integrated auxilliary functional capability equal to the functional capabilities of the auxilliary unit of FIG. 14.

FIG. 16 is an advanced auxilliary unit which when electronically linked with the embodiment of FIG. 1 can step-up the functional capabilities of the latter embodiment to attain the operational capabilities like the preferred embodiment of FIG. 9.

Since it is of utmost importance that the user be totally informed about the widely accepted normal range of values of human blood pressure and pulse rate, it is suggested here that at the back portion of each device be printed or labeled the said various normal values according to age and sex as well as the normal dynamic values during physical rest and normal physical activity, including the normal values under normal stress conditions. Also, since there are variations in the normal values dependent upon the limb location where the blood pressure and pulse rate have been measured, it is also suggested that these differential normal values be included in the normality chart.

This "Normality Chart" will have excellent worldwide utility for a self-application and application to others and will aid the greater and faster acceptance of this invention.

The recommended upper limits of normal blood pressure according to age are:
  (1) 150/100 for adults 45 years of age or older.
  (2) 135/90 for younger adults (under 45 years of age).
  (3) 120/80 being the average blood pressure for young adults.

The differences between the blood pressures between the brachial artery (upper limb) and the femoral artery (lower limb) are:
  (1) Systolic pressure of the femoral artery (supine position) ranges about 20-40 mm. Hg. higher than the systolic pressure of the brachial artery of a subject (also in a supine position).
  (2) The diastolic pressure may be lower in the femoral artery compared to the brachial artery.

The differences between the blood pressures of the right arm compared to the left arm are as follows:
  (1) The blood pressure can be 10-20 mm. Hg. higher in one arm than the other involving an inequality of either only the systolic or only the diastolic or both systolic and diastolic readings.
  (2) Approximately one fourth of the population having a measurable difference in the systolic and diastolic blood pressures between the right and left arms.
  (3) There is usually a transitory and variable difference between the left and the right arms. In certain subjects with unequal blood pressures in the two arms, the right arm has usually the higher pressure.
  (4) The blood pressure inequality in both arms may be of significant value in diagnosing the disease of the aortic arch.
  (5) If only one blood pressure measurement is to be done in the upper limb it is more accurate to rely upon the readings made in the right arm.

These values will only serve as guides and may differ from individual to individual, depending upon variations in temperature, state of health or anatomic physiopathologic environmental conditions influencing the individual.

In addition, a systematic, easy to follow, color coded, brief "Instruction Chart" will in included at the back of each device.

The front face of the device as far as groups of related function keys and displays, can be coordinated with matching color codings for easier identification and operational manipulation of the device.

It must be made clear that while the factory calibration of the invention may be based on the comparative actual equivalent optimal readings in mm. of Hg. using operation of the device because the control switch block 138 closes the electrical circuit going to the pulse rate shaping circuit 129 and the speaker control circuit 116, thus allowing the transmission of sounds and the counting of the pulses without passing through block 113. However, in the pressure measuring mode in coordination with the pulse rate measuring mode, the activation of the systolic/diastolic function key represented by number 4 of block 124, automatically commands the microprocessor 104 to open the control switch 138 so that no signal goes to block 129 and block 116.

It is important to note that no sounds will be heard through the external speaker nor the internal speaker, unless the function key numbered 2 for "SPEAKER" in block 124 has been depressed in the "ON" position no matter what mode of operation the device may be in. When the device is only in the pulse rate mode, achieved by activating the pulse rate function key numbered 5 of block 124 and the "SPEAKER" function key numbered 2 of block 124 is in the depressed "ON" position; the device can function like an electronic stethoscope and the sounds are enabled through either of the speakers, plus the capability of having a dynamic readout of the pulse rate or heart rate per minute. The sounds of the pulse beats and the heart beats including the respiratory sounds are picked up by the sound transducer 110 and the signals are directed through buffer amplifier 111 and linear amplifier 112 through the closed circuit of block 138 to the speaker control circuit 116 to the microprocessor 104 through the sound enable 117 to 116 and then to either 118 or 119. In the embodiments of the device of FIGS. 2 and 3, there can be a concurrent appearance of a pulsating LED light 63 shown in the said FIGS. 2 and 3 when the function key LED 59 is depressed in the "ON" position while the speaker function key 2 of block 124 is also in the "ON" position. Therefore, together with the speaker, the embodiments of FIGS. 2 and 3 have the audio-visual capabilities of concurrent signals of sound and light appearing respectively through either speaker and manifested by the emission of coordinating pulsating LED light 63 when detecting the pulse beats or the heart beats. In the same embodiments of FIGS. 2 and 3, when the function key "LIGHT" 60 is depressed in the "ON" position, the device can be used as a flashlight with the electric bulb 66 activated in the luminating condition.

Since the electronic block diagram of FIG. 17 is basically for the embodiment of FIG. 1, the function keys 59 and 60 for "LED" and "LIGHT" respectively, and the LED light 63 and electric bulb 66 are not shown in the said block diagram of FIG. 17.

When the calculator has been activated to function in the pressure measuring mode as well as the pulse rate measuring mode, both function keys marked Systolic/Diastolic numbered 4 and the pulse rate function key marked 5 of block 124 are depressed in the "ON" position so that the systolic and the diastolic blood pressures can be determined concurrently with the pulse rate through the detection of the Korotkoff sounds while the subjected artery such as the brachial artery is being gradually deoccluded from the state of total non-invasive occlusion secondary to the degree of compression exerted by the pressure head applying means against the aforesaid targeted vessel. The sound transducer 110 permits the detection of the associated Korotkoff sounds emitted because of the closing and gradual opening of the pressurized arterial vessel causing intra-arterial turbulent blood flow across the semi-open lumen of the vessel. The Korotkoff sounds are channeled to the buffer amplifier 111 which isolates the transducer from the internal electronics as it improves the signal condition and provides for the proper impedance matching from the transducer to the linear amplifier 112 which offers the adequate signal gain in order to drive the detector and the control circuits to achieve sufficient distinguishable rise and fall time of the audio for the proper detection of both the systolic and the diastolic levels.

The signals are then channeled to the detector and filter 113, wherein the audio is detected and then filtered in a normal method leaving a distinguishable envelope with the significant rise and decay. The signal is then transmitted to the level detector 114, wherein the detected signal becomes monitored for the distinguishable rate of increase in signal so that within milliseconds of detection the systolic enable 115 becomes activated, and then, as the signal proceeds through its decay period, the level detector evaluates each succeeding sample signal until the time that there is no change in samples determined which implies that the disappearance of the Korotkoff sounds has already been reached, activating the diastolic enable circuit 115 within milliseconds, so that the diastolic data can be latched into the proper display. The signals from the level detector 114 is sent to the systolic/diastolic and pulse enable 115 directly to the microprocessor and control circuit 104 as well as to the pulse rate shaping circuit 129. Both the systolic and the diastolic digital values are displayed in the systolic display 107 and the diastolic display 108 as enabled by 115 through the microprocessor 104. The pulse rate digital readout which is an updated dynamic value is displayed at 106 after passing through the pulse rate shaping circuit 129 through the microprocessor and control circuits 104. The systolic/diastolic and pulse enable 115 sends the pulse signals to 129 during the same time frame of systolic and diastolic blood pressures measurement, and after directing the signals to 104, the approximate LED's at the LED pressure gauge are latched successively from the systolic to the diastolic levels giving an appearance of a train of lighted LED's from the systolic level to the diastolic level located at the LED pressure display gauge. The digital values for the displays 106, 107, and 108 also become latched until a new measurement cycle is made or until the system is cleared.

When the device is in the pulse rate measuring mode, the detected audio is converted to a distinguishable square-wave pulse form which in turn becomes detected by the microprocessor as a distinguishable pulse; the succeeding pulses are measured for their pulse period thus enabling the calculator to arrive at a dynamic pulse rate measurement.

The pressure threshold setter in this case is a manually operated, 3-digit micro-switch shown in block 125 which is set by the user by turning the thumbwheels to a certain pressure level approximately thirty or more millimeters Hg. of pressure equivalence above the subject's anticipated highest systolic blood pressure. The pressure threshold set is detected by the microprocessor so that the required threshold voltage that is critical to the pressure measurement becomes set into the microcomputer's memory enabling the system to be fully activated for the proper systolic, diastolic and pulse rate measurements only after the set pressure threshold has been exceeded by the values of the pressure exerted by the pressure head applying means. This is a means of memory for future data retrieval, said physical activity delineation capable of being displayed at the main register; emotional stress function key numbered 29 which when activated in the "ON" position will be able to delineate in various switch positions as to the emotional level of the tested individual as far as either being at the low, normal, or high stress during the measuring cycle of the operation, said data can be properly displayed into the main display of the device and also capable of being entered into the microcomputer's memory through the microcomputer for future data retrieval.

It is made clear here that while some of the illustrated embodiments of the invention have concave shaped underside portions of the pressure head applying means to attain better form fitting engagement with the bicep portion portion of the arm, it is also possible that the head applying means of flattened or semi-convex underside surface of the design as shown in the embodiments of FIGS. 2 and 3 may be adapted to any of the other embodiments of the invention in order to be more useful in achieving the electronic stethoscopic functions of the device for the audio amplification of the pulse and heart sounds as well as the respiratory sounds diagnostic of certain cardiac and respiratory conditions and for determining the normality of the heart and lungs as far as good heart rhythm and respiratory air passages are concerned.

It is also possible to construct the structural framework of the device to have inter-changeable pressure head applying means depending upon the manufacturers' choice and depending upon the wide acceptance of the public.

The pressure transducer to be used is not limited only to the Hall-Effect transducer. The invention may also employ other pressure transducers of equivalent, if not better functional capabilities.

The use of the visual display for the device is not only confined to LED or LCD displays but can also employ other display means of future technological advancement which may prove to be of better efficiency and economy.

The use of the linear spring is not only limited to one spring, but a plurality of springs acting together to achieve an excellent performance for the easy compression and decompression of the device can also be employed. Other forms of mechanisms which may have spring-like action can also be incorporated.

It is important to note that although the instant invention as have been properly described and drawn in the different embodiments, additional embodiments, modification and other applications of the invention which will be obvious to those skilled in the art, are herewith included within the spirit and the scope of the invention whether it may be for current use or for future use as long as the said embodiments, modifications, and applications are within the perimeters of the present invention applied for.

What is claimed is:

1. A cuffless electronic blood pressure device including a non-circumferentially engaging pressure applying means, transducer means responsive to the compression degree of the said pressure applying means, acoustical sensor means coupled to said pressure applying means for detecting pulse rate or heart rate sounds and producing an electrical signal in response thereto, systolic signal producing means coupled to said acoustical sensor means for producing a signal representing the systolic pressure of the user, diastolic signal producing means coupled to said acoustical sensor means for producing a signal representing the diastolic pressure of the user, the systolic and diastolic signals produced being an analog representation coordinated to the analog representation of the degree of compression and decompression of the subjected tissues by the non-circumferentially engaging pressure applying means, converting means for changing said analog representation of the systolic and diastolic signals to digital visual displays thereby indicating the respective systolic and diastolic pressure of the user.

2. A cuffless electronic blood pressure device as defined in claim 1, further including pressure threshold setting means to effect conservation of electrical energy by activating the relevant electronic circuitry of the device for the desired data measurement only after the pressure exerted by the pressure applying means on the user has exceeded the pressure threshold setting.

3. A cuffless electronic blood pressure device as defined in claim 2, wherein the pressure threshold setting means is in the form of a mechanical thumbwheel.

4. A cuffless electronic blood pressure device as defined in claim 2, further including a means for logging and retrieving the data on the degree of emotional stress of the tested individual according to the date and time which the user desires to retrieve.

5. A cuffless electronic blood pressure device as defined in claim 1, further including activation means which when activated will respond to the occurence of the pulses of the Korotkoff sounds.

6. A cuffless electronic blood pressure device as defined in claim 1, further including a range locator in the pressure display wherein the approximate range between the user's systolic and diastolic blood pressure can be seen as a series of latched continuously lighted strand of LED or LCD display.

7. A cuffless electronic blood pressure device as defined in claim 1, wherein the device is of a generally rectangular hand-held form and wherein the pressure applying means extends generally axially thereto.

8. A cuffless electronic blood pressure device as defined in claim 7, further including at least one socket for the reception of an external headphone.

9. A cuffless electronic blood pressure device as defined in claim 7, further including at least one socket for the reception of a temperature indicator probe.

10. A cuffless electronic blood pressure device as defined in claim 7, further including at least one socket for the reception of a battery charger.

11. A cuffless electronic blood pressure device as defined in claim 1, wherein the non-circumferentially engaging pressure applying means is in the form of an axially displaceable piston.

12. A cuffless electronic blood pressure device as defined in claim 11, wherein the axially displaceable pressure applying means in conjunction with the pressure transducer means brings forth activation of the LED or LCD pressure display depending upon the degree of compression or decompression of the subjected artery.

13. A cuffless electronic blood pressure device as defined in claim 11, wherein the pressure applying means is a generally arcuate shape so as to conform to the shape of the subject's limb.

14. A cuffless electronic blood pressure device as defined in claim 13, further including a transparent cover for protecting the pressure applying means when not in use.

capable of retrieving said data from the memory in the form of audio, visual or a combined audio-visual registration.

39. A cuffless electronic blood pressure device as defined in claim 25, further including analog and digital display means for use in both individual or multi-individual blood pressure and pulse rate calculations, and further provided with coding means to effect proper entry of date and time data for each individual tested and retrieval capability for the respective information obtained.

40. A cuffless electronic blood pressure device as defined in claim 39, further including means for providing synthesized speech output of data and magnetic card entry and retrieval of information.

41. A cuffless electronic blood pressure device as defined in claim 25, having a function key for logging into the device the data on the physical activity level of the tested individual.

42. A cuffless electronic blood pressure device as defined in claim 25, having function keys and displays for retrieving the previously stored data on the physical activity level of the individual having been tested in conjunction with the desired date and time which the user desires to retrieve.

43. A cuffless electronic blood pressure device according to claim 25, having a function key for logging into the device the data on the degree of emotional stress of the individual being tested.

44. A cuffless electronic blood pressure device according to claim 25, having function keys and displays for retrieving the data previously stored on the degree of emotional stress of the individual having been tested in conjunction with the date and time which the user desires to retrieve.

45. A method for electronically measuring the blood pressure and pulse rate of an individual without the use of an arm encircling compression band comprising the steps of:
  (1) Gradually compressing and then gradually decompressing an axially displaceable pressure applying means having a head portion greater than the diameter of the targeted artery, positioning said head applying means approximately at a right angle position against the axis of the said targeted artery to effect a non-invasive method of occluding the subjected vessel causing total blood flow cessation across the compressed said artery and then to effect blood flow resumption with every successive cardiac contraction so as to detect the blood flow turbulence sounds known as the Korotkoff sounds by means of a sensitive acoustical transducer means located therewithin the said pressure applying means and in close proximity to the said arterial vessel for effectively detecting the systolic and the diastolic blood pressure in coordination with the degree of compression by the axially displaced pressure applying means.
  (2) axially displacing the pressure means to activate a transducer means and acoustical sensor means therewithin,
  (3) automatically converting the electrical signals from the pressure applying means which correspond to Korotkoff sounds into both analog as well as digital visual display indicating the respective systolic and diastolic pressure of the individual.

46. A method as defined in claim 45, further including the step of setting a pressure threshold which permits activation of the relevant electronic circuitry of the device for the desired data measurement of the systolic, diastolic and pulse rate only after the pressure exerted by the pressure applying means on the individual has exceeded the pressure threshold setting.

47. A method as defined in claim 46, further including the step of logging into the device, data indicating the temperature, pulse rate, limb location, time and date and ID number of the individual using the device.

48. A method as defined in claim 47, further including the step of automatically retrieving the stored data at a later time and visually displaying the same.

49. A method as defined in claim 46, further including the step of logging into the device, the current data of either the low, normal or high physical activity of the tested individual.

50. A method as defined in claim 46, further including the step of retrieving the previously stored data coordinated with either the low, normal or high level of physical activity of the tested individual according to the date and time which the user desires to retrieve.

51. A method as defined in claim 46, further including the step of logging into the device, the current data on either the low, normal or high emotional stress of the tested individual.

52. A method as defined in claim 46, further including the step of retrieving the previously stored data coordinated with either the low, normal or high emotional stress of the tested individual according to the date and time which the user desires to retrieve.

* * * * * memory for future data retrieval, said physical activity delineation capable of being displayed at the main register; emotional stress function key numbered 29 which when activated in the "ON" position will be able to delineate in various switch positions as to the emotional level of the tested individual as far as either being at the low, normal, or high stress during the measuring cycle of the operation, said data can be properly displayed into the main display of the device and also capable of being entered into the microcomputer's memory through the microcomputer for future data retrieval.

It is made clear here that while some of the illustrated embodiments of the invention have concave shaped underside portions of the pressure head applying means to attain better form fitting engagement with the bicep portion portion of the arm, it is also possible that the head applying means of flattened or semi-convex underside surface of the design as shown in the embodiments of FIGS. 2 and 3 may be adapted to any of the other embodiments of the invention in order to be more useful in achieving the electronic stethoscopic functions of the device for the audio amplification of the pulse and heart sounds as well as the respiratory sounds diagnostic of certain cardiac and respiratory conditions and for determining the normality of the heart and lungs as far as good heart rhythm and respiratory air passages are concerned.

It is also possible to construct the structural framework of the device to have inter-changeable pressure head applying means depending upon the manufacturers' choice and depending upon the wide acceptance of the public.

The pressure transducer to be used is not limited only to the Hall-Effect transducer. The invention may also employ other pressure transducers of equivalent, if not better functional capabilities.

The use of the visual display for the device is not only confined to LED or LCD displays but can also employ other display means of future technological advancement which may prove to be of better efficiency and economy.

The use of the linear spring is not only limited to one spring, but a plurality of springs acting together to achieve an excellent performance for the easy compression and decompression of the device can also be employed. Other forms of mechanisms which may have spring-like action can also be incorporated.

It is important to note that although the instant invention as have been properly described and drawn in the different embodiments, additional embodiments, modification and other applications of the invention which will be obvious to those skilled in the art, are herewith included within the spirit and the scope of the invention whether it may be for current use or for future use as long as the said embodiments, modifications, and applications are within the perimeters of the present invention applied for.

What is claimed is:

1. A cuffless electronic blood pressure device including a non-circumferentially engaging pressure applying means, transducer means responsive to the compression degree of the said pressure applying means, acoustical sensor means coupled to said pressure applying means for detecting pulse rate or heart rate sounds and producing an electrical signal in response thereto, systolic signal producing means coupled to said acoustical sensor means for producing a signal representing the systolic pressure of the user, diastolic signal producing means coupled to said acoustical sensor means for producing a signal representing the diastolic pressure of the user, the systolic and diastolic signals produced being an analog representation coordinated to the analog representation of the degree of compression and decompression of the subjected tissues by the non-circumferentially engaging pressure applying means, converting means for changing said analog representation of the systolic and diastolic signals to digital visual displays thereby indicating the respective systolic and diastolic pressure of the user.

2. A cuffless electronic blood pressure device as defined in claim 1, further including pressure threshold setting means to effect conservation of electrical energy by activating the relevant electronic circuitry of the device for the desired data measurement only after the pressure exerted by the pressure applying means on the user has exceeded the pressure threshold setting.

3. A cuffless electronic blood pressure device as defined in claim 2, wherein the pressure threshold setting means is in the form of a mechanical thumbwheel.

4. A cuffless electronic blood pressure device as defined in claim 2, further including a means for logging and retrieving the data on the degree of emotional stress of the tested individual according to the date and time which the user desires to retrieve.

5. A cuffless electronic blood pressure device as defined in claim 1, further including activation means which when activated will respond to the occurence of the pulses of the Korotkoff sounds.

6. A cuffless electronic blood pressure device as defined in claim 1, further including a range locator in the pressure display wherein the approximate range between the user's systolic and diastolic blood pressure can be seen as a series of latched continuously lighted strand of LED or LCD display.

7. A cuffless electronic blood pressure device as defined in claim 1, wherein the device is of a generally rectangular hand-held form and wherein the pressure applying means extends generally axially thereto.

8. A cuffless electronic blood pressure device as defined in claim 7, further including at least one socket for the reception of an external headphone.

9. A cuffless electronic blood pressure device as defined in claim 7, further including at least one socket for the reception of a temperature indicator probe.

10. A cuffless electronic blood pressure device as defined in claim 7, further including at least one socket for the reception of a battery charger.

11. A cuffless electronic blood pressure device as defined in claim 1, wherein the non-circumferentially engaging pressure applying means is in the form of an axially displaceable piston.

12. A cuffless electronic blood pressure device as defined in claim 11, wherein the axially displaceable pressure applying means in conjunction with the pressure transducer means brings forth activation of the LED or LCD pressure display depending upon the degree of compression or decompression of the subjected artery.

13. A cuffless electronic blood pressure device as defined in claim 11, wherein the pressure applying means is a generally arcuate shape so as to conform to the shape of the subject's limb.

14. A cuffless electronic blood pressure device as defined in claim 13, further including a transparent cover for protecting the pressure applying means when not in use.

15. A cuffless electronic blood pressure device as defined in claim 1, further including a means for logging and retrieving the data on the physical activity level of the tested individual according to the actual date and time of actual measurement.

16. A cuffless electronic blood pressure device as defined in claim 1, wherein the device is battery powered and including light or sound means to indicate either sufficient or insufficient battery power to operate the device.

17. A cuffless electronic blood pressure device as defined in claim 1, wherein the acoustical sensor means is connected to a speaker to amplify the unfiltered sounds of respiratory rales in the manner of a stethoscope.

18. A cuffless electronic blood pressure device as defined in claim 1, wherein the device is in the form of a pen-like body and wherein the pressure applying means extends generally axially thereto.

19. A cuffless electronic blood pressure device as defined in claim 1, wherein the device is in the form of a dumbbell configuration and wherein the pressure applying means extends generally axially thereto.

20. A cuffless electronic blood pressure device as defined in claim 1, including means for interconnecting said device to a temperature measuring probe and capable of displaying the temperature data of an individual or individuals according to their respective I.D. number, and capable of being stored and retrieved in accordance with the data and time of the data measurement.

21. A cuffless electronic blood pressure device as defined in claim 1, further including means for logging into the device the limb location where the blood pressure has been taken at the specific time and date, and capable of retrieving said data from the memory in the form of audio, visual or a combined audio-visual registration.

22. A cuffless electronic blood pressure device as defined in claim 1, further including analog and digital display means for use in both individual or multi-individual blood pressure and pulse rate calculations, and further provided with coding means to effect proper entry of date and time data for each individual tested and retrieval capability for the respective information obtained.

23. A cuffless electronic blood pressure device as defined in claim 22, further including means for providing synthesized speech output of data and magnetic card entry of information.

24. A cuffless electronic blood pressure device as defined in claim 1, wherein the device is battery powered and including light or sound means to indicate either sufficient or insufficient battery power to operate the device.

25. A cuffless electronic blood pressure device including a housing member adapted to be hand-held and having a displaceable piston pressure applying means generally axially oriented with respect to said housing and including transducer means responsive to the compression of the said displaceable piston, acoustical sensor means associated with said displaceable piston for detecting pulse rate or heart rate sounds and producing an electric signal in response thereto, systolic signal producing means associated with said acoustical sensor means for producing a signal representing the systolic pressure of the user, and diastolic signal producing means coupled to said acoustical sensor means for producing a signal representing the diastolic pressure of the user, the systolic and diastolic signal produced being an analog representation coordinated to the analog representation of the degrees of the compression and decompression of the subjected tissues by the displaceable piston pressure applying means, and means for converting said analog representation of the systolic and diastolic signals to digital visual displays thereby indicating the respective systolic and diastolic pressure of the user.

26. A cuffless electronic blood pressure device as defined in claim 25, further including pressure threshold setting means to effect conservation of electrical energy by activating the specific electronic circuitry of the device for optimal calculations of the desired data only after the pressure applying means on the user has exceeded the pressure threshold setting.

27. A cuffless electronic blood pressure device as defined in claim 26, wherein the pressure threshold setting means is in the form of a mechanical thumbwheel.

28. A cuffless electronic blood pressure device as defined in claim 25, further including activation means which when activated will respond to the occurrence of the pulses of the Korotkoff sounds.

29. A cuffless electronic blood pressure device as defined in claim 25, further including a range locator in the pressure display wherein the range between the user's systolic and diastolic blood pressure can be seen as a series of latched continuously lighted strand of LED or LCD display.

30. A cuffless electronic blood pressure device as defined in claim 25, wherein the axially displaceable pressure applying means in conjunction with the pressure transducer means brings forth activation of the LED or LCD pressure display depending upon the degree of compression or decompression of the subjected artery.

31. A cuffless electronic blood pressure device as defined in claim 25, wherein the pressure applying means is a generally arcuate shape so as to conform to the shape of the subject's limb.

32. A cuffless electronic blood pressure device as defined in claim 31, further including a transparent cover for protecting the pressure applying means when not in use.

33. A cuffless electronic blood pressure device as defined in claim 25, wherein the acoustical sensor means is connected to a speaker for the audio amplification of the respiratory rales in the manner of a stethoscope.

34. A cuffless electronic blood pressure device as defined in claim 25 further including at least one socket for the reception of an external headphone.

35. A cuffless electronic blood pressure device as defined in claim 25 further including at least one socket for the reception of a temperature indicator probe.

36. A cuffless electronic blood pressure device as defined in claim 25 further including at least one socket for the reception of a battery charger.

37. A cuffless electronic blood pressure device as defined in claim 25, including means for interconnecting said device to a temperature measuring probe and capable of displaying the temperature data of an individual or individuals according to their respective I.D. number, and capable of being stored and retrieved in accordance with the data and time of the data measurement.

38. A cuffless electronic blood pressure device as defined in claim 25, further including means for logging into the device the limb location where the blood pressure has been taken at the specific time and date, and capable of retrieving said data from the memory in the form of audio, visual or a combined audio-visual registration.

39. A cuffless electronic blood pressure device as defined in claim 25, further including analog and digital display means for use in both individual or multi-individual blood pressure and pulse rate calculations, and further provided with coding means to effect proper entry of date and time data for each individual tested and retrieval capability for the respective information obtained.

40. A cuffless electronic blood pressure device as defined in claim 39, further including means for providing synthesized speech output of data and magnetic card entry and retrieval of information.

41. A cuffless electronic blood pressure device as defined in claim 25, having a function key for logging into the device the data on the physical activity level of the tested individual.

42. A cuffless electronic blood pressure device as defined in claim 25, having function keys and displays for retrieving the previously stored data on the physical activity level of the individual having been tested in conjunction with the desired date and time which the user desires to retrieve.

43. A cuffless electronic blood pressure device according to claim 25, having a function key for logging into the device the data on the degree of emotional stress of the individual being tested.

44. A cuffless electronic blood pressure device according to claim 25, having function keys and displays for retrieving the data previously stored on the degree of emotional stress of the individual having been tested in conjunction with the date and time which the user desires to retrieve.

45. A method for electronically measuring the blood pressure and pulse rate of an individual without the use of an arm encircling compression band comprising the steps of:
(1) Gradually compressing and then gradually decompressing an axially displaceable pressure applying means having a head portion greater than the diameter of the targeted artery, positioning said head applying means approximately at a right angle position against the axis of the said targeted artery to effect a non-invasive method of occluding the subjected vessel causing total blood flow cessation across the compressed said artery and then to effect blood flow resumption with every successive cardiac contraction so as to detect the blood flow turbulence sounds known as the Korotkoff sounds by means of a sensitive acoustical transducer means located therewithin the said pressure applying means and in close proximity to the said arterial vessel for effectively detecting the systolic and the diastolic blood pressure in coordination with the degree of compression by the axially displaced pressure applying means.
(2) axially displacing the pressure means to activate a transducer means and acoustical sensor means therewithin,
(3) automatically converting the electrical signals from the pressure applying means which correspond to Korotkoff sounds into both analog as well as digital visual display indicating the respective systolic and diastolic pressure of the individual.

46. A method as defined in claim 45, further including the step of setting a pressure threshold which permits activation of the relevant electronic circuitry of the device for the desired data measurement of the systolic, diastolic and pulse rate only after the pressure exerted by the pressure applying means on the individual has exceeded the pressure threshold setting.

47. A method as defined in claim 46, further including the step of logging into the device, data indicating the temperature, pulse rate, limb location, time and date and ID number of the individual using the device.

48. A method as defined in claim 47, further including the step of automatically retrieving the stored data at a later time and visually displaying the same.

49. A method as defined in claim 46, further including the step of logging into the device, the current data of either the low, normal or high physical activity of the tested individual.

50. A method as defined in claim 46, further including the step of retrieving the previously stored data coordinated with either the low, normal or high level of physical activity of the tested individual according to the date and time which the user desires to retrieve.

51. A method as defined in claim 46, further including the step of logging into the device, the current data on either the low, normal or high emotional stress of the tested individual.

52. A method as defined in claim 46, further including the step of retrieving the previously stored data coordinated with either the low, normal or high emotional stress of the tested individual according to the date and time which the user desires to retrieve.

* * * * *